(12) United States Patent
Hashimoto

(10) Patent No.: US 6,500,118 B1
(45) Date of Patent: Dec. 31, 2002

(54) THREE-DIMENSIONAL ULTRASONIC DIAGNOSTIC APPARATUS

(75) Inventor: Shinichi Hashimoto, Tochigi (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/425,206

(22) Filed: Oct. 22, 1999

(30) Foreign Application Priority Data

Oct. 23, 1998 (JP) .......................................... 10-302975

(51) Int. Cl.[7] ................................................ A61B 8/00
(52) U.S. Cl. ........................ 600/437; 600/443; 128/916
(58) Field of Search ................................ 600/437, 427, 600/443, 424, 447, 453, 463; 128/916; 367/7, 11, 130; 73/625, 626; 382/305; 712/38; 345/177, 179, 419

(56) References Cited

U.S. PATENT DOCUMENTS

| | | | | |
|---|---|---|---|---|
| 5,476,096 A | * | 12/1995 | Olstad et al. | ............... 128/916 |
| 5,568,811 A | * | 10/1996 | Olstad | ........................ 128/916 |
| 5,588,434 A | * | 12/1996 | Fujimoto | ................... 600/443 |
| 5,645,066 A | * | 7/1997 | Gandini et al. | ............. 600/443 |
| 5,871,019 A | * | 2/1999 | Belohlavek | ................. 128/916 |
| 6,110,118 A | * | 8/2000 | Guracar et al. | ............. 600/453 |
| 6,169,817 B1 | * | 1/2001 | Parker et al. | ............... 345/419 |
| 6,204,853 B1 | * | 3/2001 | Cline et al. | ................. 345/419 |

* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

An ultrasonic diagnostic apparatus including a three-dimensional scanner for carrying out a three-dimensional scanning by ultrasonic waves. The apparatus also includes a three-dimensional image data former for forming three-dimensional image data based on scanning data obtained from the three-dimensional scanner. An image data memory is included as part of the apparatus for storing in time series a plurality of pieces of three-dimensional image data formed by the three-dimensional image data former. The apparatus includes a memory controller for controlling write and read of the three-dimensional image data into or from the image data memory. And the apparatus further includes a display image former for forming a display image based on three-dimensional image data read out from the image data memory by the memory controller, and for displaying the formed display image on a display unit.

26 Claims, 12 Drawing Sheets

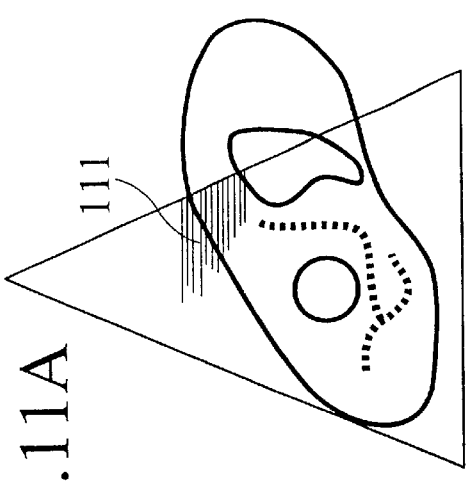
FIG.11B
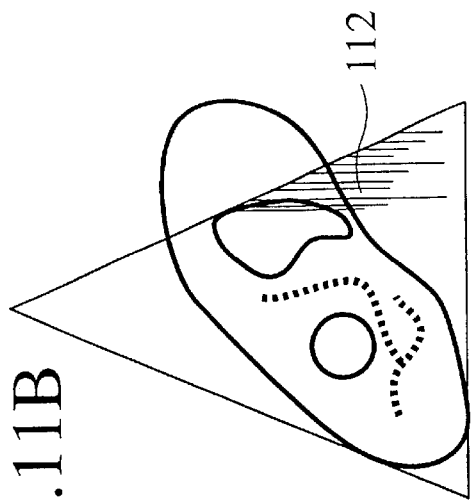
FIG.11A
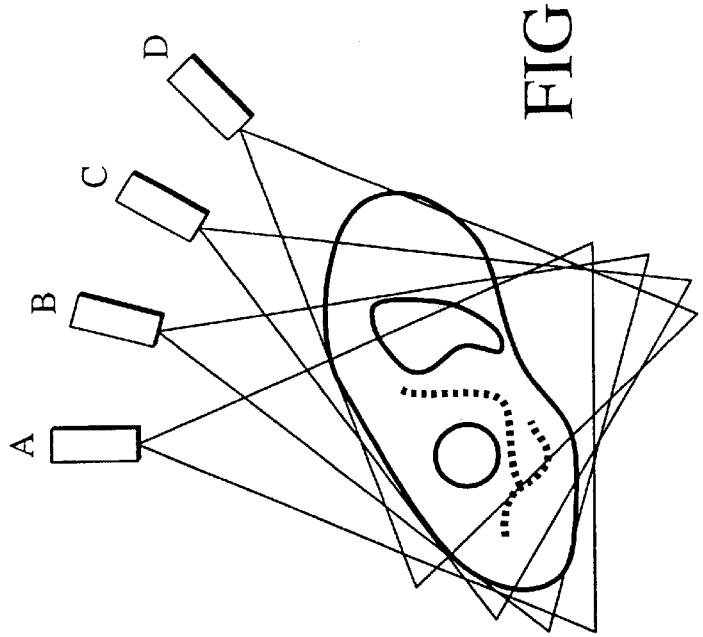
FIG.11E
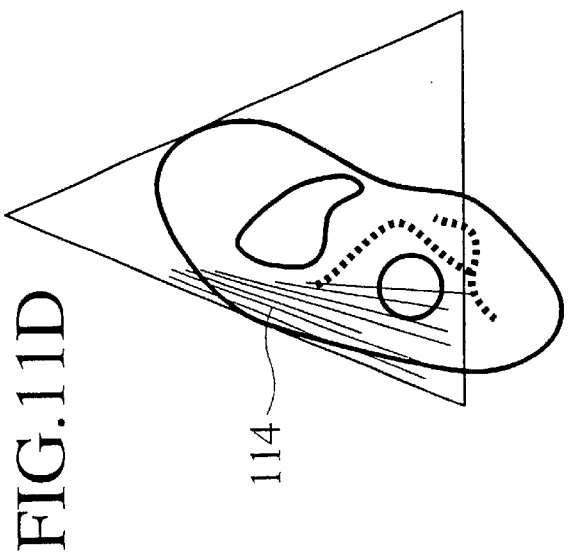
FIG.11C
FIG.11D

THREE-DIMENSIONAL ULTRASONIC DIAGNOSTIC APPARATUS

BACKGROUND OF THE INVENTION

1. Field of the Invention

The present invention relates to a three-dimensional ultrasonic diagnostic apparatus. More particularly, the present invention relates to an image memory technique for easily achieving many varieties of three-dimensional image analyses under arbitrary display conditions for volume data obtained in the past, by storing an obtained volume data in a loop memory in time series in a real-time three-dimensional ultrasonic diagnostic apparatus for carrying out an acquisition and display of the volume data in real time.

2. Description of the Background Art

A two-dimensional ultrasonic diagnostic apparatus conventionally utilized employs a system for displaying a tomographic image obtained by scanning one tomographic plane by an ultrasonic wave beam. In the mean time, in recent years, there have been carried out various trials of three-dimensional ultrasonic diagnosis for obtaining three-dimensional image data (that is, volume data) by acquiring diagnostic images while moving an ultrasonic probe that is an ultrasonic transceiver in a three-dimensional ultrasonic diagnostic apparatus. Thus, there has been placed a large expectation in a potential of a new diagnosis based on a three-dimensional image in this three-dimensional ultrasonic diagnostic apparatus. More particularly, researches have been progressed which is concerning the use of a manually or mechanically moving a convex probe or a linear-arrayed probe for abdomen or a multi-plane probe through esophagus having a function of rotating an electronic sector probe.

Particularly, there have recently been progressed researches and developments on a real-time three-dimensional ultrasonic diagnostic apparatus for acquiring and displaying three-dimensional information in real time, by electronically carrying out a three-dimensional scanning by ultrasonic waves at high speed. In other words, this real-time three-dimensional ultrasonic diagnostic apparatus is an apparatus for sequentially displaying volume data that is three-dimensional image data acquired.

The above-described three-dimensional ultrasonic diagnostic apparatus, however, has the following problems.

This real-time three-dimensional ultrasonic diagnostic apparatus is still at a research stage, and fundamentals including a detailed method of achieving this apparatus or utilizing the apparatus have not yet been established.

According to the above-described two-dimensional ultrasonic diagnostic apparatus, as tomographic image data acquired by ultrasonic waves is simply displayed as a two-dimensional image, the tomographic image displayed and the acquired data basically correspond to each other at 1 to 1. Therefore, by merely storing the acquired image data itself on the image memory, it is easy to analyze the past data of image displayed in the past, by displaying of this past data again.

In this conventional two-dimensional ultrasonic diagnostic apparatus, the past image is an image data itself acquired in the past. For example, although there has been a technique for separately storing a plurality of kinds of images such as B mode images, Doppler images like CFM, M mode images, etc., these kinds of images are basically two-dimensional image data respectively. Therefore, there has never been a case of displaying images quite different from the images displayed in the past.

As a technique that can be used for storing the above-described past record of image data, there is available a cine-memory replay technique. This cine-memory is a loop-structured memory (loop memory) for storing data arranged in time array by sequentially updating the data at prescribed time intervals. This technique is disclosed in, for example, Japanese Patent Application Laid-open Publication No. Hei 3-210247.

On the other hand, according to the above-described three-dimensional ultrasonic diagnostic apparatus, it is not possible to display all the acquired three-dimensional image data (hereinafter to be referred to as volume data) on an image display unit (a cathode-ray tube, CRT). Therefore, it is necessary to image-process these volume data and display the processed result on a two-dimensional CRT as a three-dimensional display image. In other words, as compared with the two-dimensional ultrasonic diagnostic apparatus, the conventional three-dimensional ultrasonic diagnostic apparatus, particularly the real-time three-dimensional ultrasonic diagnostic apparatus for scanning ultrasonic image information three-dimensionally at high speed as not an acquisition of tomogpraphic images but as one volume data, and displaying the scanned result by sequentially processing the images, has a characteristic that the three-dimensional image data acquired by ultrasonic waves does not correspond to the displayed three-dimensional image data at 1 to 1.

Therefore, the above-described three-dimensional ultrasonic diagnostic apparatus has a problem that it is possible to display only limited three-dimensional data when only the displayed three-dimensional image data is used as the past image. The above-described memory for storing only the displayed image data has not been sufficient for a three-dimensional ultrasonic system.

Further, generally, at the time of carrying out an ultrasonic diagnosis, an image is displayed by always changing display conditions of the image in order to perform an optimum analysis of the image displayed.

Therefore, particularly in the case of observing a moving tissue such as a blood stream of a subject (that is, human body under examination), or in the case of observing a display image by moving it, the conventional three-dimensional ultrasonic diagnostic apparatus has a problem that it requires a frequent complex operation for adjusting display conditions each time an image displayed in the past is replayed, making it difficult to replay the past images.

In other words, a method of displaying a three-dimensional image with respect to three-dimensional image data is theoretically limitless. It has, therefore, been required to obtain a new technique for achieving a function of replaying a past image from the viewpoint of display conditions of identifying an angle and conditions from which an object to be diagnosed is observed as a three-dimensional image.

SUMMARY OF THE INVENTION

The present invention has been made to solve the above-described problems of the conventional technique. It is an object of the present invention to provide a three-dimensional ultrasonic diagnostic apparatus capable of displaying past three-dimensional display images retroactively to a prescribed past time, by keeping a record of volume data in a memory system of a loop memory (cine-memory) structure that stores data of time-series array by sequentially updating the data at prescribed time intervals.

Further, it is another object of the present invention to achieve a replay of a past three-dimensional display image can be achieved in an easy operation, by storing in the loop memory display conditions of the three-dimensional display image formed from the stored volume data. It may be so structured that a display condition of the past three-dimensional display image can be arbitrarily selected according to the need of desired analysis, from among a display condition based on the past display and a currently-set display condition.

Therefore, it is possible to carry out in an easy operation various three-dimensional image analyses retroactively to the past images based on the past volume data record. Furthermore, it is possible to carry out a three-dimensional image analysis at high speed and in high precision.

According to one aspect of the present invention, as shown in FIG. 1, there is provided an ultrasonic diagnostic apparatus, comprising:

a three-dimensional scanner (1, 2, 3) for carrying out a three-dimensional scanning by ultrasonic waves; a three-dimensional image data former 4 for forming three-dimensional image data based on scanning data obtained from the three-dimensional scanner; a three-dimensional image data memory 5 for storing in time series a plurality of pieces of three-dimensional image data formed by the three-dimensional image data former; a memory controller 6 for controlling write and read of the three-dimensional image data into or from the three-dimensional image data memory; and a display image former for forming a display image based on three-dimensional image data read out from the three-dimensional image data memory by the memory controller, and for displaying the formed display image on a display unit.

According to another aspect of the present invention, as shown in FIG. 2, there is provided an ultrasonic diagnostic apparatus, comprising:

a three-dimensional scanner (1, 2, 3) for carrying out a three-dimensional scanning by ultrasonic waves; a three-dimensional image data former 4 for forming three-dimensional image data based on scanning data obtained from the three-dimensional scanner; a three-dimensional image data memory 5 for storing in time series a plurality of pieces of three-dimensional image data formed by the three-dimensional image data former; a display condition data memory 10 for storing in time series a plurality of pieces of display condition data for forming the three-dimensional display image, the display condition data being corresponding to each of the tree-dimensional image data; a memory controller 62 for controlling write and read of the three-dimensional image data and the display condition data into or from the three-dimensional image data memory and the display condition data memory; and a display image former 7 for forming a display image based on three-dimensional image data read out from the three-dimensional image data memory and display condition data read out from the display condition data memory by the memory controller, and for displaying the formed display image on a display unit.

The apparatus shown in FIG. 2 may further comprise a display condition selector for selecting either the display condition data used in the past for forming a three-dimensional display image based on the three-dimensional image data or currently-set display condition data, according to a user's instruction; wherein, the display image former forms a display image based on the read-out three-dimensional image data, based on display condition data selected by the display condition selector.

The display condition information may include at least one of a direction of a probe to a subject, opacity, color information added to a Doppler image, and a threshold value for extracting an area of the subject.

The above-described apparatus may further comprise a display image memory 15 for storing in time series a plurality of the display images, the display image being corresponding to the three-dimensional image data, as shown in FIG. 3.

The above-described apparatus may further comprise, as shown in FIG. 5, a position data generator 31 for generating probe position data according to a position of the three-dimensional scanner; and a position data memory 32 for storing in time series the probe position data obtained from the position data generator with making the probe position data correspond to each of the three-dimensional image data stored in the three-dimensional image data memory.

In this case, the display image former 7 may be structured to form a display image of a wider range than that of each of the three-dimensional image data by connecting a plurality of pieces of three-dimensional image data stored in the three-dimensional image data memory, according to the probe position data.

Alternatively, the display image former 7 may be structured to form a display image with corrected image quality of each three-dimensional image data by combining a plurality of pieces of three-dimensional image data stored in the three-dimensional image data memory, according to the probe position data.

Alternatively, the display image former 7 may also be structured to calculate a relative position for indicating what portion of a subject a display image corresponds to, according to reference position data for indicating a position of the three-dimensional scanner set on the subject and the probe position data, and to display an indicator for indicating the relative position based on the calculated relative position together with the display image.

Other features and advantages of the present invention will become apparent from the following description taken in conjunction with the accompanying drawings.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 11A, 11B, 11C, 11D and 11E are views for explaining one example of a display of a connection of portions of satisfactory image quality among a plurality of image data pieces according to the fifth embodiment of the present invention;

DETAILED DESCRIPTION OF THE PREFERRED EMBODIMENTS

Embodiments of a three-dimensional ultrasonic diagnostic apparatus according to the present invention will be explained in detail below with reference to the drawings.

First Embodiment

According to a first embodiment, as an image data memory system in a three-dimensional ultrasonic diagnostic apparatus, a memory system having a structure of what is called a four-dimensional array (memory) is employed for continuously storing acquired three-dimensional image data (hereinafter to be referred to as volume data) itself in time series, instead of storing display image data in the image data memory system.

With this arrangement, there is provided a function of performing a variety of three-dimensional image analyses, by easily reconstructing a variety of three-dimensional display images with respect to acquired past three-dimensional image data.

Figure 1:
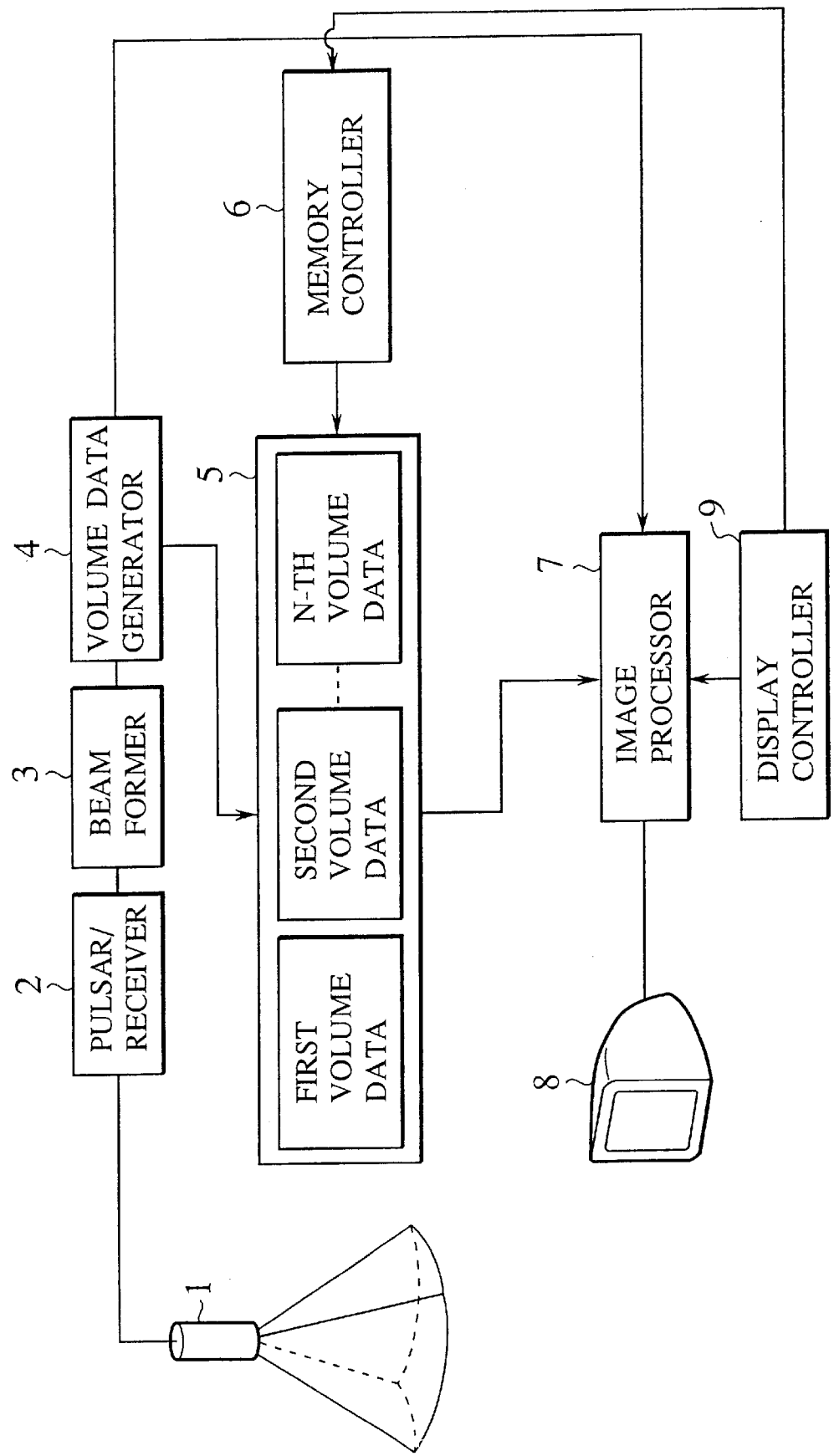
FIG. 1 is a block diagram for showing a structure of a three-dimensional ultrasonic diagnostic apparatus according to a first embodiment of the present invention.

FIG. 1 is a block diagram for showing a structure of a three-dimensional ultrasonic diagnostic apparatus according to the first embodiment of the present invention. As shown in FIG. 1, the three-dimensional ultrasonic diagnostic apparatus according to the first embodiment comprises a three-dimensional ultrasonic probe 1 for carrying out a three-dimensional scanning by ultrasonic-wave beams, a pulsar/receiver 2 for transmitting an ultrasonic wave and receiving reflection waves of ultrasonic wave by the three-dimensional ultrasonic probe 1, a beam former 3 for forming acquired data by waveform-shaping the reflection waves received by the pulsar/receiver 2, a volume data generator 4 for generating three-dimensionally acquired image data (that is, volume data) based on the acquired data formed by the beam former 3, a four-dimensional volume memory 5 for sequentially storing in time-series the volume data generated by the volume data generator 4, a memory controller 6 for controlling write and read of volume data into and from the four-dimensional volume memory 5, an image processor 7 for forming a three-dimensional display image based on the volume data read out from the four-dimensional volume memory 5, a display unit 8 for displaying a three-dimensional display image formed by the image processor 7, and a display controller 9 for inputting and controlling display conditions of a three-dimensional image displayed on this display unit 8. A two-dimensional array probe or a mechanical scan probe can be used as the three-dimensional probe.

In above configuration, the four-dimensional volume memory 5 is structured by applying the above-described technique of cine-memory (loop memory). By using this loop memory, it is possible to obtain the past three-dimensional display image through effective utilization of memory resources.

Next, the process procedure of the three-dimensional ultrasonic diagnostic apparatus according to the first embodiment having the above-described configuration will be explained.

At first, the three-dimensional ultrasonic probe 1 has a two-dimensional array shape having a plurality of ultrasonic-wave elements laid out in a matrix, and this probe 1 can scan the subject by ultrasonic waves in a box shape, for example, at one time.

The pulsar/receiver 2 sends an driving pulse for transmitting the ultrasonic wave to the three-dimensional ultrasonic probe 1, based on a transmitting signal sent from beam former 3. After the transmission of the ultrasonic wave, an ultrasonic echo signal received by the three-dimensional ultrasonic probe 1 is amplified and sent to the beam former 3.

The beam former 3 generates a transmitting signal and provides the signal to the pulsar/receiver 2, the signal being delayed so that the ultrasonic beam is sent in the prescribed scan line direction.

In this case, the beam former 3 generates the ultrasonic echo signal by delay and adding processing as the ultrasonic echo on the prescribed scan line is to be obtained with respect to the ultrasonic echo of each ultrasonic transducer element which is sent from the pulsar/receiver 2. And the beam former 3 scans the three-dimensional area while changing the scan line direction sequentially.

Note that so-called parallel simultaneous receiving should be carried out in which a plurality of ultrasonic echo signals on a plurality of scan lines with respect to one ultrasonic wave transmission for fast scan in three-dimensional area.

The volume data generator 4 generates three-dimensional image data (volume data) based on the ultrasonic echo signal, and supplies this volume data to the four-dimensional volume memory 5 and the image processor 7.

The volume data may have a box shape, for example, or may have various other shapes. In this case, basically, the volume data is assumed to be added with data capable of specifying a position of a scannable range of the boxes of the corresponding data (that is, a range where data to be analyzed exists).

The image processor 7 reconstructs a three-dimensional display image based on the volume data when the volume data is supplied from the volume data generator 4, and displays this reconstructed image on the display unit (CRT)

8. Thus, the display unit 8 can display the three-dimensional display image in real time.

On the other hand, when the volume data from the volume data generator 4 is supplied to the four-dimensional volume memory 5, the memory controller 6 controls the sequential writing into the four-dimensional volume memory 5, of each of a plurality of volume data (that is, first volume data, second volume data, . . . -, n-th volume data: where n represents a natural number) sequentially generated in time series in the volume data generator 4, as shown in FIG. 1.

The memory controller 6 controls the sequential writing of each volume data as explained above. In more detail, the four-dimensional volume memory 5 has areas for storing a plurality (n pieces) of volume data respectively, and each volume data sequentially generated in the volume data generator 4 is stored in each of these areas in sequence. In this case, when there has come no memory area (that is, when the memory area has been saturated) in the four-dimensional volume memory 5, the memory controller 6 controls the writing of the four-dimensional volume memory 5 so that the oldest volume data is replaced with the latest volume data. In this time, the memory controller 6 controls the writing by identifying the latest data with a pointer or the like.

In other words, the memory controller 6 controls the writing of each volume data in the order of first volume data, second volume data, . . . , and n-th volume data, into the four-dimensional volume memory 5 in times series at prescribed time intervals, unless otherwise particularly instructed by the operator, to thereby control the writing of n volume data into the four-dimensional volume memory 5. When the memory areas of the four-dimensional volume memory 5 have been saturated, the memory controller 6 controls to write the next (n+1)-th volume data into the memory area where the first volume data has been written, and write the (n+2)-th volume data into the memory area where the second volume data has been written. In other words, the memory controller 6 carries out a write control of the four-dimensional volume memory 5 as the above-described loop memory (cine-memory). With this arrangement, each of a plurality of volume data acquired during a prescribed time interval is stored in each area of the four-dimensional volume memory 5. This four-dimensional volume memory 5 is updated to the latest status by overwriting, that is, by writing the latest volume data on the oldest volume data among the stored volume data.

Next, the memory controller 6 reads out the latest volume data from among the volume data written in the four-dimensional volume memory 5, and supplies this latest volume data to the image processor 7.

Alternatively, the memory controller 6 reads out volume data designated by the operator through the display controller 9, from among volume data written in the four-dimensional volume memory 5, and supplies this designated volume data to the image processor 7. The image processor 7 carries out a prescribed three-dimensional image processing to the volume data read out from the four-dimensional volume memory 5, and forms a three-dimensional display image. The image processor 7 then supplies this three-dimensional display image to the display unit 8 to display this three-dimensional display image.

Based on an input by the operator, the display controller 9 sends a signal for controlling the three-dimensional display image that is displayed on the display unit 8, to the image processor 7. More specifically, when there has been a designation of volume data from the operator, the display controller 9 requests the memory controller 6 to read the corresponding volume data. The volume data read out is three-dimensionally image-processed by the image processor 7, and the result is displayed on the display unit 8. At the time of a real-time display, the display controller 9 makes the operator input display conditions to be described later by suitably changing the conditions so that the three-dimensional display image currently displayed is optimized to facilitate the analysis.

Further, when there has been an input of an instruction for freezing a real-time display, for example, from the operator, the display controller 9 interrupts a screen output processing (a real-time display processing) for sequentially displaying the latest image. When the operator instructs a replay of a past image by using a track ball or the like, for example, the past three-dimensional display image is replayed based on the volume data stored in the four-dimensional volume memory 5.

According to the above-described procedure, a past three-dimensional display image desired by the operator can be easily reconstructed and displayed on the display unit 8, based on arbitrary past volume data read out from the four-dimensional volume memory 5.

Each area for storing each volume data of the four-dimensional volume memory 5 can be structured by dividing the area into a plurality of (for example, two) sub-areas (memory areas). When a subject (that is, human body under examination) includes a moving tissue such as a blood stream, for example, tomographic image information in a static status of the tissue of the object (that is, gray scale image information) is stored in the first sub-area, and moving information of the tissue (that is, Doppler information) is stored in the second sub-area, respectively. With this arrangement, it is possible to reconstruct a tomographic plane image for an easy analysis of the image, in structuring a three-dimensional display image by adding colors of red and blue, for example, to the blood stream of the tissue.

As explained above, according to the three-dimensional ultrasonic diagnostic apparatus according to the first embodiment, the volume data generator 4 forms three-dimensional image data (volume data), and the four-dimensional volume memory 5 sequentially stores these volume data in time series. For replay of an image, the image processor 7 reconstructs the three-dimensional display image based on the volume data stored on the four-dimensional volume memory 5, and displays this image. Thus, it is possible to easily reconstruct a three-dimensional display image under various display conditions viewed from a desired direction, based on the past volume data, in the three-dimensional ultrasonic diagnostic apparatus. Accordingly, the three-dimensional ultrasonic diagnostic apparatus according to the first embodiment can greatly contribute to the diversification and facilitation of three-dimensional image analysis that has been strongly desired so far.

Second Embodiment

Next, a three-dimensional ultrasonic diagnostic apparatus according to a second embodiment of the present invention will be explained in detail with reference to FIG. 2. The three-dimensional ultrasonic diagnostic apparatus according to the second embodiment provides a function of storing in a loop memory display condition data that indicates from which direction and how a three-dimensional display image is displayed on the display unit 8, the display condition data corresponding to each volume data. By this correspondence, it is always possible to display in an easy operation a three-dimensional image displayed under the same display condition as that of a three-dimensional image displayed in the past.

Figure 2:
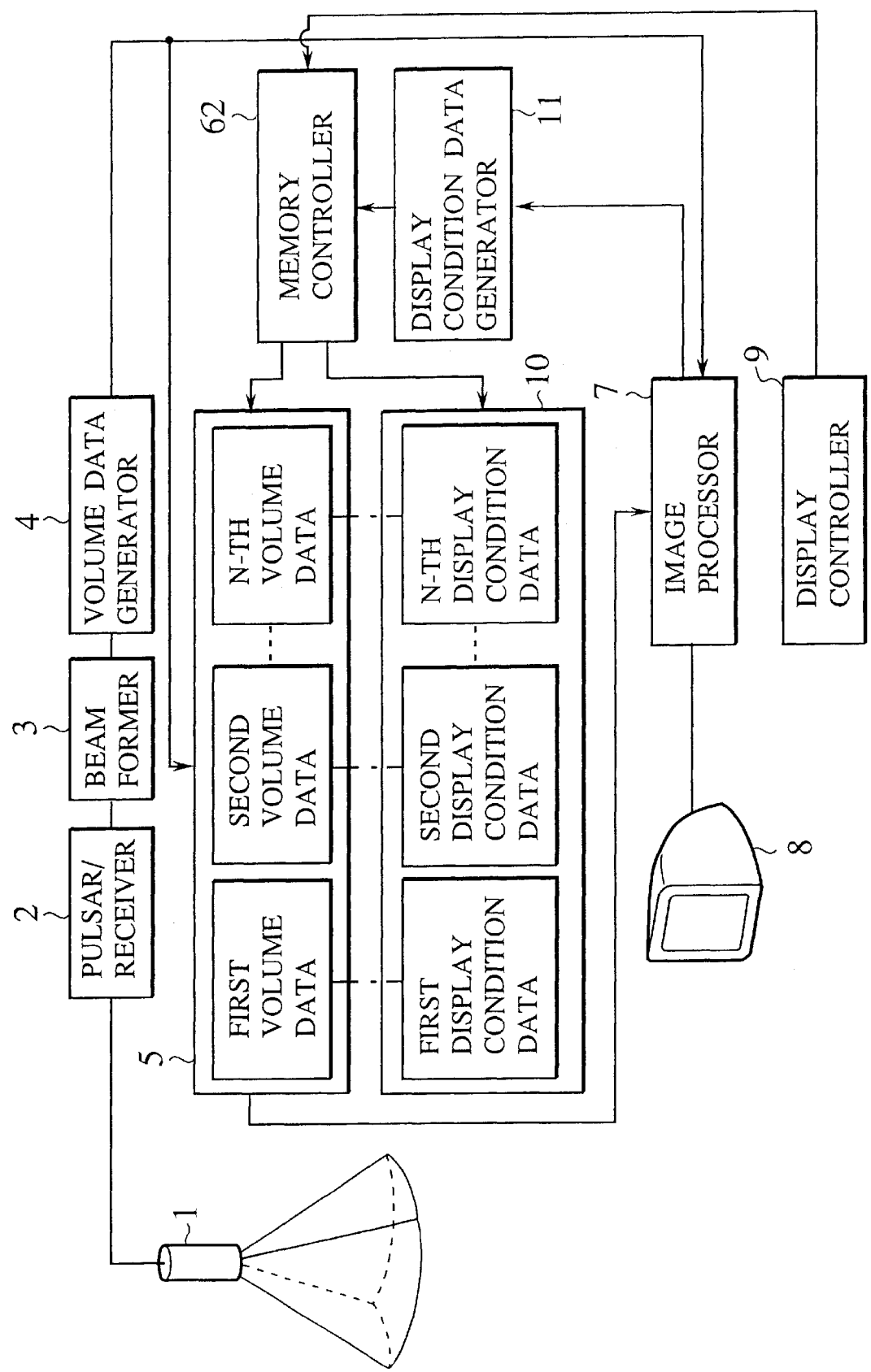
FIG. 2 is a block diagram for showing a structure of a three-dimensional ultrasonic diagnostic apparatus according to a second embodiment of the present invention.

FIG. 2 is a block diagram for showing a structure of a three-dimensional ultrasonic diagnostic apparatus according to the second embodiment of the present invention.

As shown in FIG. 2, the three-dimensional ultrasonic diagnostic apparatus according to the second embodiment is a modification of the first embodiment in that, in addition to the three-dimensional ultrasonic diagnostic apparatus according to the first embodiment shown in FIG. 1, the apparatus includes, as shown in FIG. 2, a display condition data memory 10 for storing a plurality of pieces of display condition data corresponding to each volume data and a display condition data generator 11 for forming display condition information that indicates display conditions set in a three-dimensional display image displayed on the display unit 8, and that the memory controller 6 in FIG. 1 is replaced with a memory controller 62 for writing/reading to/from the display condition data memory 10. As the second embodiment is different from the first embodiment in only the above points, description will be made hereinafter of only these differences, and a duplicated explanation will be omitted. In FIG. 2, those units attached with reference symbols identical with those in FIG. 1 provide similar functions as those of the corresponding units of the same reference symbols.

Here, the display condition data is the information for indicating from which direction and how the three-dimensional image displayed on the display unit 8 has been displayed. This display condition data is formed based on the information set in the image processor 7 in the past when the three-dimensional display image was formed based on the corresponding volume data. The operator can input an instruction to the display controller 9, the instruction indicating the past point of timing in which display condition data is to be stored. This display condition data includes, for example, a direction of a viewpoint when a subject is observed, opacity of a tomographic plane image, additional color information at the time of adding a color to a part of acquired data such as a Doppler image or the like, a threshold value, etc. This direction of the viewpoint is obtained as the direction of the three-dimensional ultrasonic probe 1. Further, this threshold value is, for example, a prescribed CT value, and is used for a processing for extracting a certain area from an image, for example, for setting a certain part of the acquired data such as a tissue in the subject as non-display mode to facilitate the analysis.

Each volume data in the four-dimensional volume memory 5 and the display condition data corresponding to this. volume data may be corresponded to each other according to an arbitrary method. For example, both the volume data and the display condition data may hold time stamps, and the volume data and the display condition data with matched time stamps may be read out by the memory controller 6. Alternatively, by arranging the number of the memory areas of the four-dimensional volume memory 5 equal to the number of the memory areas of the display condition data memory 10, it becomes easy to obtain a correspondence between n-th volume data and the corresponding n-th display condition data, by simply using the number (order) of the memory area. For this purpose, it is desirable that the number of the memory areas for storing each display condition data of the display condition data memory 10 is structured the same as the number of the memory areas for storing each volume data of the four-dimensional volume memory 5.

It is also desirable that the display condition data memory 10 is structured as the above-described loop memory.

Next, the process procedure of the three-dimensional ultrasonic diagnostic apparatus according to the second embodiment will be explained. The operations of the three-dimensional ultrasonic probe 1, the pulsar/receiver 2, the beam former 3 and the volume data generator 4 are similar to those of the first embodiment.

When a three-dimensional display image of the latest volume data 3 is formed by the image processor 7 and the image is displayed on the display unit 8 as described above, the display condition data generator 11 forms display condition data (first display condition data, second display data, and n-th display condition data) for indicating from which direction and how the volume data corresponding to the three-dimensional image displayed on the display unit 8 is formed, and supplies this formed display condition data to the memory controller 62. The memory controller 62 writes this display condition data to the display condition data memory 10 with making this display condition data correspond to each volume data stored in the four-dimensional volume memory 5.

Next, when the display of a three-dimensional display image of certain volume data has been instructed from the display controller 9, the memory controller 6 reads out from the display condition data memory 10 display condition data corresponding to the volume data of which display has been instructed. Simultaneously, the memory controller 6 reads out from the four-dimensional volume memory 5 volume data corresponding to this display condition data, and supplies this volume data to the image processor 7.

The image processor 7 forms a three-dimensional display image based on the read-out volume data and the corresponding display condition data, and supplies this three-dimensional display image to the display unit 8. The display unit 8 displays this three-dimensional display image supplied.

According to the second embodiment, the following effects can be obtained.

Even when display conditions for displaying a three-dimensional display image are changing every moment, it is possible to replay the three-dimensional display image under the display condition under which the corresponding volume data was displayed in real time in the past. Therefore, it becomes possible to easily replay and display the three-dimensional image displayed in the past in a simple operation, without involving a complex image adjusting operation again for analyzing the image at the time of replay of the past image. Accordingly, this can further facilitate a three-dimensional image analysis.

Third Embodiment

Next, a three-dimensional ultrasonic diagnostic apparatus according to a third embodiment of the present invention will be explained in detail with reference to FIG. 3.

The above-described three-dimensional ultrasonic diagnostic apparatus according to the second embodiment is for storing display condition data for indicating a display setting of a three-dimensional image displayed on the display unit 8 in the display condition data memory 10 structured as a loop memory, with making this display condition data correspond to each volume data. On the other hand, the three-dimensional ultrasonic diagnostic apparatus according to the third embodiment provides a function of storing in the image memory a three-dimensional display image itself displayed in real time on the display unit 8, with making this three-dimensional display image correspond to each volume data. By storing the past three-dimensional display image, it is possible to replay the past three-dimensional display image at high speed, without involving an image reconstruction again.

Figure 3:
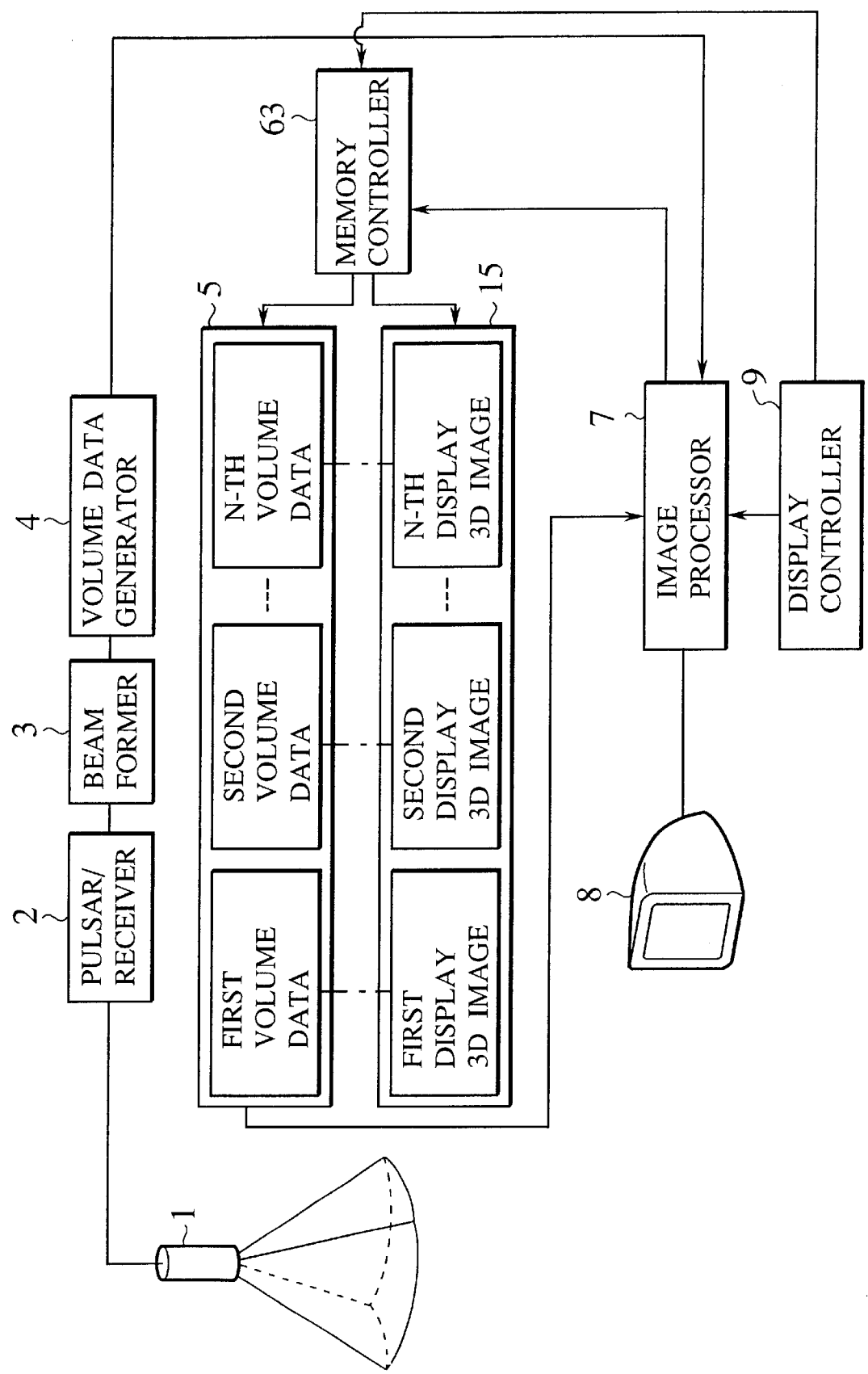
FIG. 3 is a block diagram for showing a structure of a three-dimensional ultrasonic diagnostic apparatus according to a third embodiment of the present invention.

FIG. 3 is a block diagram for showing a structure of the three-dimensional ultrasonic diagnostic apparatus according to the third embodiment of the present invention.

The three-dimensional ultrasonic diagnostic apparatus according to the third embodiment is a modification of the first embodiment in that, as compared with the first embodiment shown in FIG. 1, the apparatus further includes, as shown in FIG. 3, a display image memory 15 for storing a three-dimensional image displayed on the display unit 8, with making the three-dimensional display image correspond to each volume data stored in the four-dimensional volume memory 5, and that the memory controller 6 in FIG. 3 is replaced with a memory controller 63 for further writing/reading to/from the display image memory 15. As the third embodiment is different from the first embodiment in only the above points, description will be made hereinafter of only these differences, and a duplicated explanation will be omitted. In FIG. 3, those units attached with reference symbols identical with those in FIG. 1 provide similar functions as those of the corresponding units of the same reference symbols.

Next, the process procedure of the three-dimensional ultrasonic diagnostic apparatus according to the third embodiment will be explained. The operations of the three-dimensional ultrasonic probe 1, the pulsar/receiver 2, the beam former 3 and the volume data generator 4 are similar to those of the first embodiment.

As shown in FIG. 3, when a three-dimensional display image has been formed by the image processor 7 based on the latest volume data stored in the four-dimensional volume memory 5, the memory controller 63 controls the writing of the three-dimensional display image itself in the display image memory 15 with making this three-dimensional display image correspond to the volume data stored in the four-dimensional volume memory 5.

It is desirable that this display image memory 15 is structured as the above-described loop memory. In writing to this display image memory 15, this memory controller 6 carries out a write control similar to the write control to the four-dimensional volume memory 5. In other words, when the memory areas of the display image memory 15 have been saturated, the memory controller 6 controls the writing to write the latest three-dimensional display image on the oldest three-dimensional display image. At the same time, the memory controller 6 controls the writing so as to be able to identify the latest three-dimensional display image, in a similar manner to the first embodiment.

As explained above, when the display of the past three-dimensional display image has been instructed by the display controller 9, the three-dimensional display image written in the display image memory 15 is read out by the memory controller 6 and is displayed on the display unit 8 through the image processor 7.

According to the third embodiment, the following effects can be obtained.

The three-dimensional ultrasonic diagnostic apparatus according to the third embodiment uses both a memory system for continuously storing volume data in the time axis and an image memory system for continuously storing a displayed three-dimensional display image in the time axis. Therefore, in the case of replay of a three-dimensional image displayed in real time in the past, it is possible to read out the corresponding three-dimensional display image from this display image memory 15 and display this three-dimensional display image on the display unit 8, without image-processing again the volume data in the four-dimensional volume memory 5. Accordingly, it is possible to replay at high speed a desired three-dimensional image displayed in the past under the same display condition as that for the past display. In the case of displaying a three-dimensional display image under a display condition different from that for the three-dimensional image displayed in the past, the three-dimensional display image may be formed in the manner as explained in the first embodiment, based on the corresponding volume data stored in the four-dimensional volume memory 5.

Fourth Embodiment

Next, a three-dimensional ultrasonic diagnostic apparatus according to a fourth embodiment of the present invention will be explained in detail with reference to FIG. 4.

The above-described three-dimensional ultrasonic diagnostic apparatus according to the second embodiment is for storing display condition information for indicating a display setting of a three-dimensional image displayed on the display 8 in the display condition data memory 10 with making this display condition information correspond to each volume data. The three-dimensional ultrasonic diagnostic apparatus according to the third embodiment is for storing in the image memory 15 a three-dimensional display image itself displayed on the display unit 8, with making this three-dimensional display image correspond to each volume data. On the other hand, the three-dimensional ultrasonic diagnostic apparatus according to the fourth embodiment has both the display condition data memory 10 and the display image memory 15, and provides a function of storing both the display condition data and the three-dimensional display image itself displayed in real time on the display unit 8, with making this display condition data and this three-dimensional display image correspond to each volume data.

Figure 4:
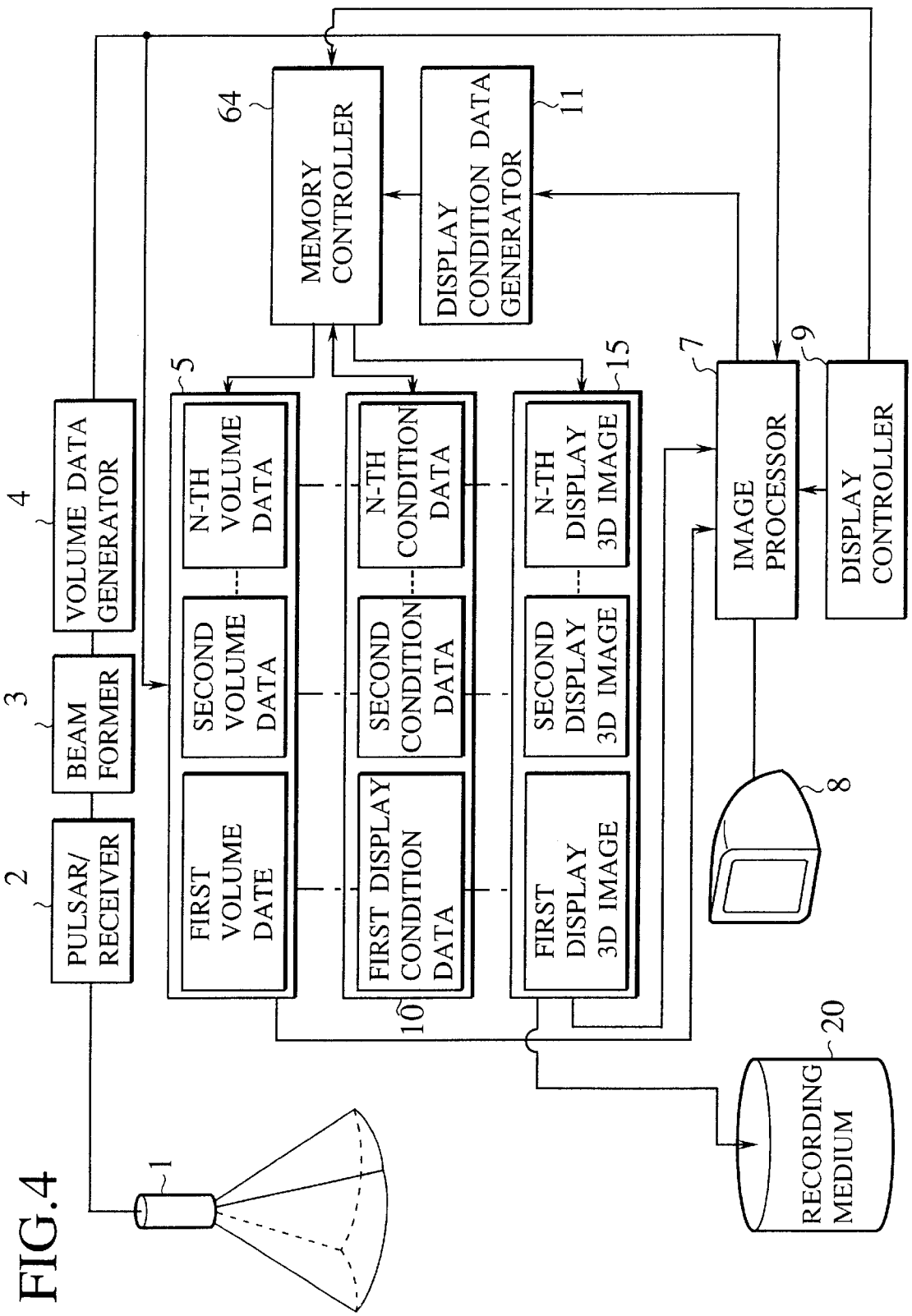
FIG. 4 is a block diagram for showing a structure of a three-dimensional ultrasonic diagnostic apparatus according to a fourth embodiment of the present invention.

FIG. 4 is a block diagram for showing a structure of the three-dimensional ultrasonic diagnostic apparatus according to the fourth embodiment of the present invention.

The three-dimensional ultrasonic diagnostic apparatus relating to the fourth embodiment is a modification of the aforementioned embodiments in that, in addition to the first embodiment shown in FIG. 1, the apparatus includes, as shown in FIG. 4, the display condition data memory 10 for storing the display condition data that indicates display conditions of the three-dimensional image displayed on the display unit 8, the display condition data generator 11 for forming this display condition data based on the information supplied from the image processor 7, and the display image memory 15 for storing the three-dimensional display image itself displayed on the display unit 8 provided in the third embodiment shown in FIG. 3, and that the memory controller 6 in FIG. 3 has been replaced with a memory controller 64 for writing/reading to from both the display condition data memory 10 and the display image memory 15. As the fourth embodiment is different from the above embodiment in only the above points, description will be made hereinafter of only these differences, and a duplicated explanation will be omitted. In FIG. 4, those units attached with reference symbols identical with those in FIG. 1 to FIG. 3 provide similar functions as those of the corresponding units of the same reference symbols.

Next, the process procedure of the three-dimensional ultrasonic diagnostic apparatus according to the fourth embodiment will be explained. The operations of the three-dimensional ultrasonic probe 1, the pulsar/receiver 2, the beam former 3 and the volume data generator 4 are similar to those of the above embodiment.

In FIG. 4, when a three-dimensional display image of the latest volume data 3 is formed by the image processor 7 and the image is displayed on the display unit 8 as described above, the display condition data generator 11 forms display condition data (first display condition data, second display condition data, . . . , and n-th display condition data) for indicating from which direction and how the volume data corresponding to the three-dimensional image displayed on the display unit 8 is formed, and supplies this formed display condition data to the memory controller 64.

The memory controller 64 writes this display condition data to the display condition data memory 10 with making this display condition data correspond to each volume data stored in the four-dimensional volume memory 5.

When the display of a three-dimensional display image based on certain volume data in the four-dimensional volume memory 5 has been instructed, the memory controller 64 reads out display condition data from the display condition data memory 10. At the same time, the memory controller 64 reads out the instructed volume data from the four-dimensional volume memory 5, and supplies this volume data to the image processor 7. The image processor 7 forms a three-dimensional display image based on this volume data and the corresponding display condition data, and displays the formed three-dimensionally displayed image on the display unit 8.

When a three-dimensional display image has been formed by the image processor 7 based on the latest volume data stored in the four-dimensional volume memory 5, the memory controller 64 controls the writing of the formed three-dimensionally displayed image in the display image memory 15 with making this three-dimensional display image correspond to the volume data stored in the four-dimensional volume memory 5. In controlling the writing to this display image memory 15, the memory controller 64 controls the writing so that the. latest three-dimensional display image is written on the oldest three-dimensional display image, when the memory areas of display image memory 15 have been saturated, in a manner similar to the write control to the four-dimensional volume memory 5. At the same time, the memory controller 64 controls the writing to the display image memory 15 so as to be able to identify the latest three-dimensional display image.

As explained above, when the display of the past three-dimensional display image has been instructed by the display controller 9, the three-dimensional display image written in the display image memory 15 is read out by the memory controller 64 and is displayed on the display unit 8.

According to the fourth embodiment, the following effects can be obtained. Even when display conditions for displaying a three-dimensional display image in real-time display are changing every moment, it is possible to easily replay the three-dimensional display image under the display condition under which the corresponding volume data was displayed in the past, based on the display condition data used for the display in the past and the corresponding volume data.

On the other hand, in the case of replay of the three-dimensional image displayed in real time in the past, it is possible to read the corresponding three-dimensional display image from this display image memory 15 and display it on the display unit 8. Therefore, it is possible to replay at high speed a desired three-dimensional image displayed in the past.

Further, in the case of forming a three-dimensional display image from the past volume data by newly setting complex display conditions, it is possible to continuously carry out the forming of the three-dimensional display image at high speed.

As explained above, the three-dimensional ultrasonic diagnostic apparatus according to the fourth embodiment has all of the four-dimensional volume memory 5, the display condition data memory 10 for storing display condition data that indicates a display setting of the three-dimensional image displayed on the display unit 8, and the display image memory 15 for storing the three-dimensional display image itself displayed on the display unit 8. Therefore, it is easy to replay a highly complex three-dimensional display image that is difficult to be displayed in real time as a continuous image, by using continuous volume data and display condition data corresponding to this volume data or a three-dimensional display image.

More specifically, it is possible to easily replay continuously a high-level three-dimensional image such as, for example, a volume rendering image and a surface rendering image which are shadow processed, a wire frame image, a flythrough image, etc. Further, as explained in the second embodiment and the third embodiment, it is also possible to easily replay retroactively an image itself displayed in real time in the past.

Further, the three-dimensional ultrasonic diagnostic apparatus according to each of the embodiments of the present invention can record a continuously replayed image in an external recording system (a recording medium) such as, for example, a magnetic recording medium 20, as shown in FIG. 4. With this arrangement, it is possible to store. the volume data according to the need, before the oldest volume data of the loop memory is overwritten. Particularly, a large number of volume data is required for recording and replaying three-dimensional moving image data. Therefore, by utilizing the external recording system as well as the incorporated recording system, it is possible to analyze easily the move of the three-dimensional moving image data at certain time intervals.

Fifth Embodiment

Next, a three-dimensional ultrasonic diagnostic apparatus according to a fifth embodiment of the present invention will be explained in detail with reference to FIG. 5 to FIG. 14.

The three-dimensional ultrasonic diagnostic apparatus according to the fifth embodiment includes a position detecting mechanism for detecting a position of a three-dimensional ultrasonic probe 1, and provides a function of storing three-dimensional position data of each volume data based on a detected position detected by this mechanism, and of carrying out various three-dimensional image processing based on the stored position data. This position data can be used for correcting positional coordinates in the display of a formed three-dimensional display image, for example.

Figure 5:
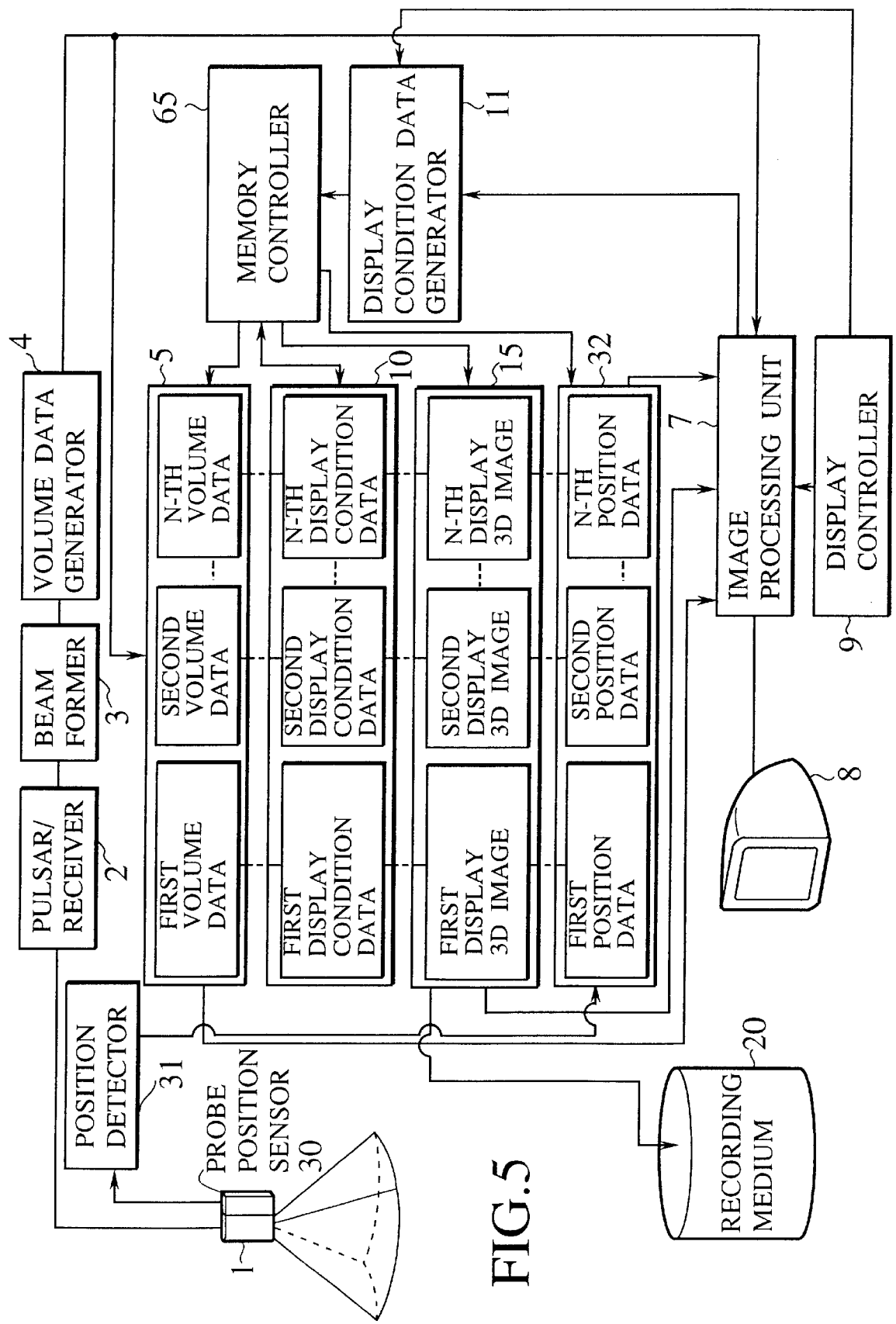
FIG. 5 is a block diagram for showing a structure of a three-dimensional ultrasonic diagnostic apparatus according to a fifth embodiment of the present invention.

FIG. 5 is a block diagram for showing a structure of a three-dimensional ultrasonic diagnostic apparatus according to the fifth embodiment of the present invention.

The three-dimensional ultrasonic diagnostic apparatus according to the fifth embodiment is a modification of the fourth embodiment in that, as compared with the fourth embodiment shown in FIG. 4, the apparatus further includes, as shown in FIG. 5, a probe position sensor 30 for detecting a position of the three-dimensional ultrasonic probe 1, a position detector 31 for collecting position information from the probe position sensor 30, and a position data memory 32 for storing position data (first position data, second position data, . . . , and n-th position data) collected with the position detector 31 with making this collected data correspond to each volume data stored in the four-dimensional volume memory 5, and that the memory controller 64 of the fourth embodiment shown in FIG. 4 is further replaced with a memory controller 65 for writing/reading to/from position data memory 32. Description will be made hereinafter of only these differences between the fifth embodiment and the above embodiments, and a duplicated explanation will be omitted. In FIG. 5, those units attached with reference symbols identical with those in FIG. 4 provide similar functions as those of the corresponding units of the same reference symbols shown in FIG. 4.

At first, the position detecting mechanism in the fifth embodiment will be explained. Among many systems considered for this position detecting mechanism, two systems will be explained hereunder.

A first system is a system for carrying out a position detection by the probe position sensor 30 which is incorporated in or mounted on the three-dimensional ultrasonic probe 1. There are many embodiments of achieving this probe position sensor. For example, it is possible to use a magnetic probe position sensor, an optical probe position sensor and an ultrasonic probe position sensor. Position data collected by the probe position sensor 30 is stored within a memory of the ultrasonic diagnostic apparatus.

A second system is a system for carrying out a position detection by using volume data (three-dimensional image data) acquired in real time from the ultrasonic diagnostic apparatus, by not using a probe position sensor. The three-dimensional ultrasonic diagnostic apparatus according to the present invention is based on the acquisition of volume data at intervals of about a few volumes to several tens of volumes per second. On the other hand, in most cases, the three-dimensional ultrasonic probe 1 is moved manually by the operator. When the three-dimensional ultrasonic probe 1 is moved while acquiring volume data, the acquired image is volume data of a part continuous in time series. Accordingly, when volume data at a certain point of time is compared with volume data before or after this point of time, the same part makes a slight move in the image. In other words, the image data obtained has a relatively high correlation.

In this case, with volume data at a certain specific time used as reference data, orthogonal three-directional azimuth axes (X, Y, Z) are defined, and a move volume of what is called six degrees of freedom are calculated to indicate in which direction and to what degree the same part has moved and to which axis and to what degree this part has moved. When this calculated result is used as position data, it is possible to specify a relative position of the image with respect to the reference three-dimensional image. This position data can be stored in the position data memory 32. This position data corresponds to probe position data in the claims.

Next, the process procedure of the three-dimensional ultrasonic diagnostic apparatus according to the fifth embodiment will be explained. The operations of the three-dimensional ultrasonic probe 1, the pulsar/receiver 2, the beam former 3 and the volume data generator 4 are similar to those of the above embodiment.

In the three-dimensional ultrasonic diagnostic apparatus according to the fifth embodiment, the probe position sensor 30 detects a position of the three-dimensional ultrasonic probe 1, and supplies this position data to the position detector 31. Alternatively, the position detector 31 may calculate position information based on the move volume of the six free degrees by using the above-described second system, without providing the probe position sensor 30.

The position detector 31 collects position data from the probe position sensor 30, and supplies this position data to the position data memory 32.

The memory controller 65 controls the writing into the position data memory 32 of the position data collected by the position detector 31, with making this collected position data correspond to each volume data stored in the four-dimensional volume memory 5. It is desirable that this position data memory 32 is structured as the above-described loop memory.

In forming a new three-dimensional display image from each volume data stored in the four-dimensional volume memory 5, the memory controller 65 reads out position data corresponding to the three-dimensional display image to be formed newly from the position data memory 32, and supplies this read-out position data to the image processor 7.

Figure 6A:
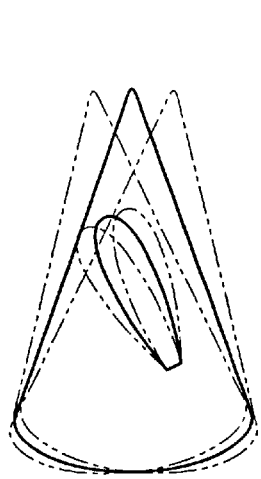
FIGS. 6A and 6B are views for explaining an example of a correction processing to be carried out by an image processing unit according to the fifth embodiment of the present invention.
Figure 6B:
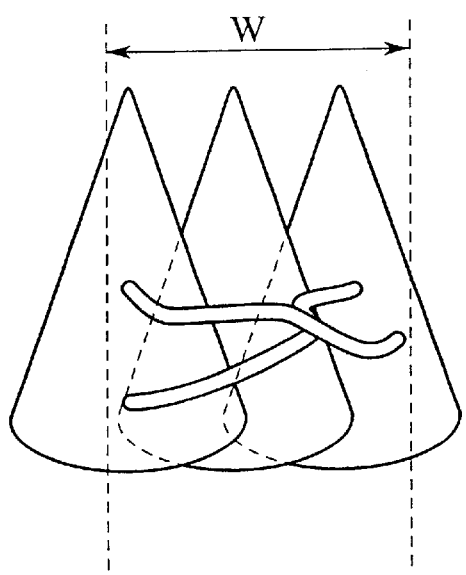

The image processor 7 calculates mutual positional relationship between a plurality. of volume data based on the position data read out from the position data memory 32, forms a three-dimensional display image after correcting a three-dimensional positional relationship necessary for a three-dimensional image display, and displays this corrected three-dimensional display image on the display unit 8. More specifically, for correcting the three-dimensional positional relationship, there are, for example, "display correction" for correcting mutual positional deviation between volume data derived from a move of the three-dimensional ultrasonic probe 1 due to the deviation of the three-dimensional ultrasonic probe by hand, as shown in FIG. 6A, and "expansion display" for correcting a mutual positional deviation between volume data in the case of obtaining a three-dimensional display image by observing a tissue over a wide range W, as shown in FIG. 6B.

Next, there will be explained below detailed examples of showing a three-dimensional display image by using volume data stored in a time-series layout in the four-dimensional volume memory 5 and position data corresponding to each volume data.

A first display example is an example for showing a three-dimensional display image over a wide range by connecting volume data acquired continuously and stored in the memory.

The operator sequentially acquires volume data while moving the three-dimensional ultrasonic probe 1 capable of acquiring volume data at high speed, at low speed on a part to be observed. In this case, a position detection of a three-dimensional display image is also carried out by using the position detecting mechanism. The acquired volume data is reconstructed as a three-dimensional display image, and this image is displayed on the display unit 8. In this case, it is possible to display a plurality of continuous volume data as a three-dimensional display image by connecting the plurality of volume data in high precision by using the position data.

Detailed examples of methods of the above-described connection of volume data will be explained below.

A first method is a most simple connection method. At first, a plurality of continuously acquired volume data are laid out based on the position data. The continuous volume data include mutually overlapping portions. Therefore, at first, non-overlapped portions are selected with priority placed on data at the past side of the time axis. A plurality of the selected data are then sequentially connected.

Figure 7:
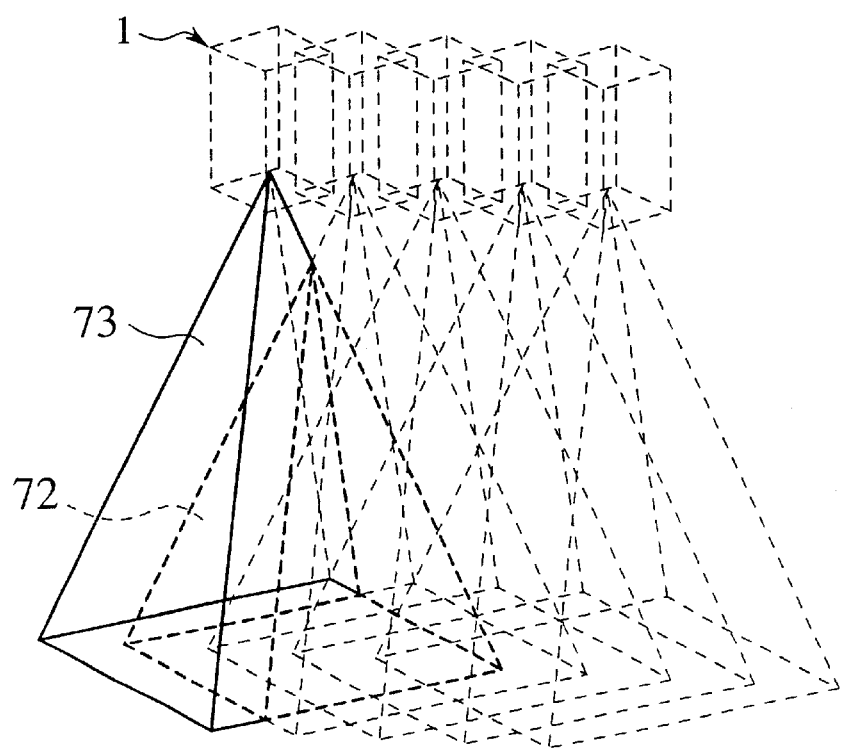
FIG. 7 is an explanatory view for showing one example of a display of a connection of image data according to the fifth embodiment of the present invention.

FIG. 7 shows an example of this first connection method. FIG. 7 shows a status that the volume data acquired by moving the three-dimensional ultrasonic probe I are laid out based on the position data. Each volume data is divided into a portion 72 (a broken-line portion) which is overlapped with an adjacent image of a new image on the time axis and a non-overlapped portion 73 (a solid-line portion). By sequentially connecting only the non-overlapped portions 73, it is possible to prepare three-dimensional display image of a wide range. In preparing the display image, the display may be carried out based on the connected three-dimensional image data (volume data), or the display may be carried out by connecting the three-dimensional display images themselves prepared based on each volume data. For connecting volume data, many other methods than the above can be applied.

In the case of connecting volume data based on the above-described first method, in some cases, it is not possible to sufficiently obtain continuity in the connected images when the precision of position detection is low. This is because as non-overlapped three-dimensional areas are sequentially connected, errors in position detection causes deviation in the images of the connected portions.

Figure 8A:
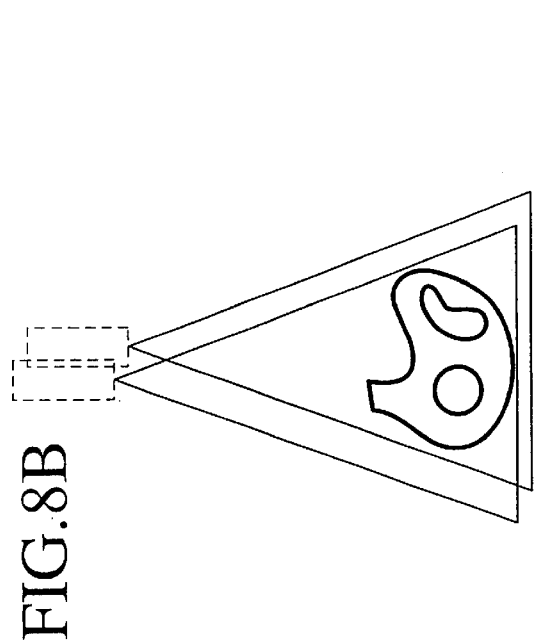
FIGS. 8A and 8B are views for explaining one example of a processing of correcting a deviation of images in the connection processing in FIG. 7.
Figure 8B:
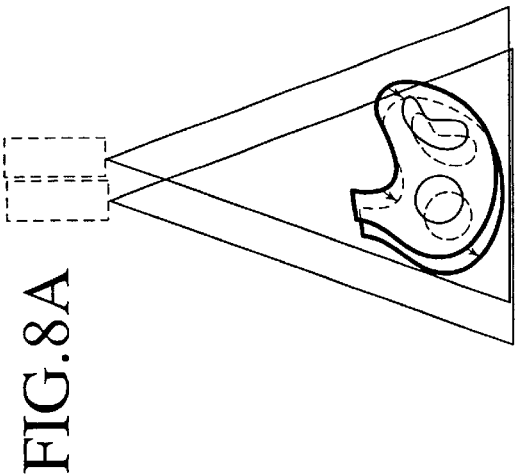

This deviation in the images can be corrected as follows based on common characteristics of the image data. First, image data of the overlapped portions are compared, and then positions are corrected so that the respective image data are most overlapped. FIG. 8A schematically shows a status that there have been generated deviations in the images. This positional deviation can be corrected as shown in FIG. 8B by correcting position data so that the image data coincide most.

Figure 9A:
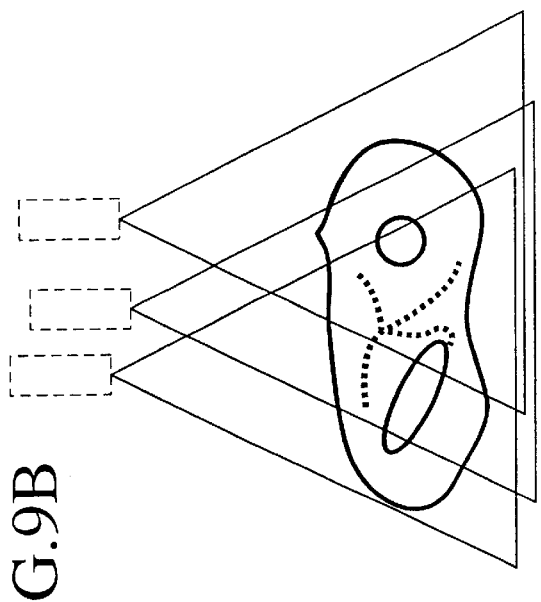
FIGS. 9A and 9B are views for explaining another example of a processing of correcting a deviation of images in the connection processing in FIG. 7.
Figure 9B:
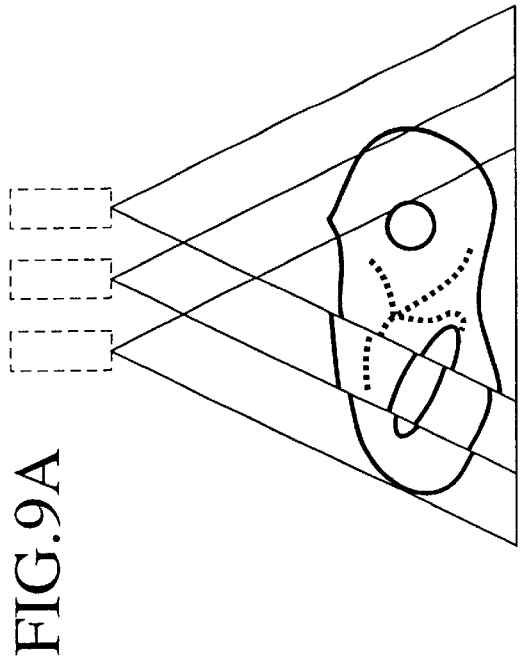

Alternatively, there is a second correcting method. According to this method, continuity of the image data at connected portions is detected, and the position data is corrected to have a high continuity. FIG. 9A shows a status that the continuity of the images is lost due to the positional deviation. In this case, when positions are corrected to have a high continuity in three portions (1, 72, 73) shown in FIG. 7 so as to form a continuous image at the connected portions, an image after the positional correction is obtained as shown in FIG. 9B. This positional correction can be carried out by detecting a correction position where the images of a connection plane are the most similar in form, for example. By correcting the deviation of the images, it is possible to carry out a connection of volume data or three-dimensional display images in high precision. Note that FIGS. 8A and 8B and FIGS. 9A and 9B are shown as two-dimensional images to facilitate the understanding, it is also possible to apply this in three-dimensional images in a similar manner. Further, the above-described positional correction can also be similarly applied to the conventional ultrasonic diagnostic apparatus handling two-dimensional images.

Further, there is also a third method of connecting volume data by fixing the image acquisition to one specific cross section of a three-dimensional scanning area by the ultrasonic probe 1 and by sequentially detecting the cross-sectional positions. In this case, it is necessary to carry out positional detection frequently at very high speed. On the other hand, as only one plane is required for an ultrasonic scanning plane, there are advantages that a high-quality image can be obtained and that the ultrasonic probe 1 itself may be a normal probe for two-dimensional scanning not limited to a probe capable of scanning three-dimensionally.

Figure 10B:
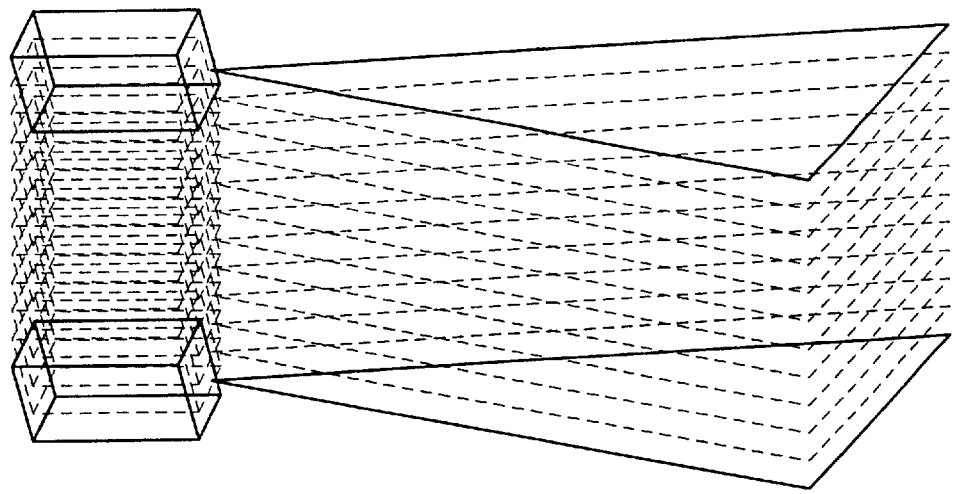
FIGS. 10A and 10B are explanatory views for showing another example of a display of a connection of a plurality of image data pieces according to the fifth embodiment of the present invention.
Figure 10A:
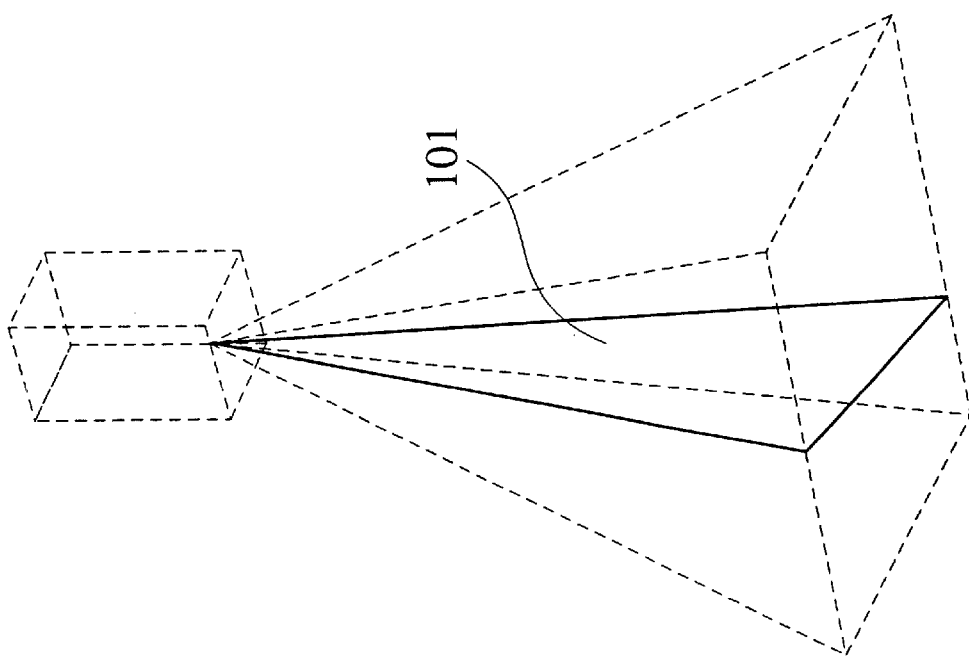

Further, as each one cross section is connected, it is possible to obtain continuity of images. FIGS. 10A and 10B show a concept of this third connection method. As shown in FIG. 10A, at first, any one arbitrary cross section 101 is selected from out of a three-dimensionally scannable range that can be scanned by the probe 1. Next, as shown in FIG. 10B, cross sections are connected sequentially based on a position data obtained by moving the probe 1, so that three-dimensional data can be obtained. This three-dimensional data naturally includes reformatted data such as the data re-sampled after the connection.

When the above-described connection methods are used, it is possible to display a three-dimensional ultrasonic image of a wide range by utilizing position data.

Also, the above-described connection methods may be applied to the conventional ultrasonic diagnostic apparatus concerning the two-dimensional image.

Next, a second display example is an example of carrying out a corrected display for making volume data higher quality by utilizing the position data of the volume data. This method is to cope with a problem that an ultrasonic image is easily disturbed by various factors. These various factors include, for example, a rib or a calcified tissue, a shadow due to a gas or the like inside a digestive tract, a clatter noise due to a pulsation of the heart or a breathing operation at the time of a color Doppler display, a phase distortion due to an abdominal wall, a focusing deviation derived from a personal difference of speed distribution, etc. These factors of image deterioration are the problems that cannot be easily improved, as the factors are derived from the basic principle of the ultrasonic image.

There also arises a case where it is not possible to obtain a satisfactory image due to the above-described factors in the conventional ultrasonic diagnostic apparatus using a normal ultrasonic probe, not limited to the three-dimensional ultrasonic probe 1. However, particularly when a three-dimensional display image is acquired by pressing a three-dimensionally scannable ultrasonic probe 1 to a target part inside a subject, above mentioned factors arise more frequent influences in the image quality as the scanning area is a wide range. When such an image deterioration has been observed, generally a position at which the ultrasonic probe 1 is applied is changed, and a direction in which the target part can be observed satisfactorily is searched. However, it is general that there is no such a direction in which all the portions of the target part can be observed satisfactorily. Therefore, generally, the observer (operator) must arrange an image from various directions in mind, and decide a direction.

In the second display example, the fifth embodiment has such an arrangement that volume data is corrected to volume data of a satisfactory image quality by using a plurality of volume data of a target part observed from different directions and position data of the volume data. More particularly, the target part is observed from a plurality of directions (that is, volume data are acquired), and these volume data are combined based on the position data of images. Satisfactory parts of the images are connected at overlapped portions, to form one combined volume data (three-dimensional image data), thereby to reconstruct a three-dimensional display image.

FIG. 11 schematically illustrates this method. Each of image data 11A, 11B, 11C and 11D which are the image data of the same part observed from different directions respectively has suffered some image deterioration (111, 112, 113, 114). When only the portions not suffering image deterioration are extracted from out of the image data 11A, 11B, 11C and 11D, and image data of the portions are corrected in position by using position data, it is possible to obtain a three-dimensional display image of high image quality as represented by 11E. In this. case, it is necessary to have means for deciding what image of what portion is of good quality at the overlapped portions. As a simple method of making a decision of image quality, there is a method that the observer (the operator) selects an area and an image. There is also another selection method that an overlapped area as a whole is divided into small areas, then the frequency of image data in each divided small area is analyzed, and the data with the highest frequency component is selected. Based on these methods, it is possible to obtain a satisfactory three-dimensional image even in an area where an overall image cannot be displayed clearly by a normal method.

A third display example is an example of utilizing position data of three-dimensional image data (volume data) as a body mark for indicating a part of a human body that is being observed. According to the conventional ultrasonic diagnostic apparatus, an ultrasonic probe is pressed against the surface of the body to display a two-dimensional tomographic image. Therefore, the body mark for identifying what part of the human body is being displayed as an image indicating a relative position on the subject including rough information of the part of the body and the direction in which the probe is applied. As this body mark is recorded at the same time when the display image data is recorded, it is possible to understand to some extent the body mark information when the image is observed at a later stage.

On the other hand, in the three-dimensional ultrasonic diagnostic apparatus, it is possible to reconstruct a three-dimensional display image of an arbitrary direction or an arbitrary tomographic image from the acquired data. Therefore, the conventional body mark has a problem that it is difficult to understand about what part of the body an image is currently displaying and from which direction this part has been observed. This problem becomes more conspicuous as various image processing is carried out by a post processing based on the acquired data. In order to solve this problem, it is desirable that a body mark is attached to all the image data acquired. However, in actual practice, it is difficult for the operator to add manually additional information to each piece of data in the three-dimensional ultrasonic diagnostic apparatus that acquires a large number of volume data (three-dimensional image data) at high speed.

Thus, in the third display example, the fifth embodiment is arranged such that a marking is made at a reference acquisition point, such as, for example, at the time of the starting of the data acquisition, and thereafter, the body mark is sequentially displayed indicating which part of the body is, based on a relative position information calculated using the position data of the image. As it is possible to identify volume data (three-dimensional image data) about to what part of the body and from which direction an ultrasonic probe has been applied, it is possible to identify a three-dimensional display image formed based on this position data or an arbitrary tomographic image about from what part of the body has been observed and from which direction this part has been observed.

A detailed procedure of the third display example will be explained. At first, the operator starts image acquisition by pressing the ultrasonic probe 1 of the three-dimensional ultrasonic diagnostic apparatus having a position detecting mechanism against a body surface portion. Next, by halting the move of the ultrasonic probe 1 as far as possible, body mark data is corresponded to position data. More specifically, the operator inputs through the display controller 9 information about what position and which direction of the subject the position data being collected corresponds to. In this time, information about which direction and pose the subject stays is to be inputted as an instruction by the operator in advance. Thereafter, the image processor 7 calculates a relative positional relationship between the newly collected position data and the corresponded position data (reference position data), and decide about what part of the body is being observed and from which direction this part is being observed. The image processor 7 suitably displays a body mark for showing what part of the body is being observed and from which direction this part is being observed for each of the three-dimensional display image. Based on the above-described procedure, in the three-dimensional ultrasonic diagnostic apparatus for displaying a three-dimensional display image in real time or by post processing, it is possible to automatically update the display of the body mark each time when the display of the three-dimensional display image is updated, without requiring an input of body mark each time. Accordingly, it becomes possible to understand a three-dimensional display image more easily.

Figure 12:
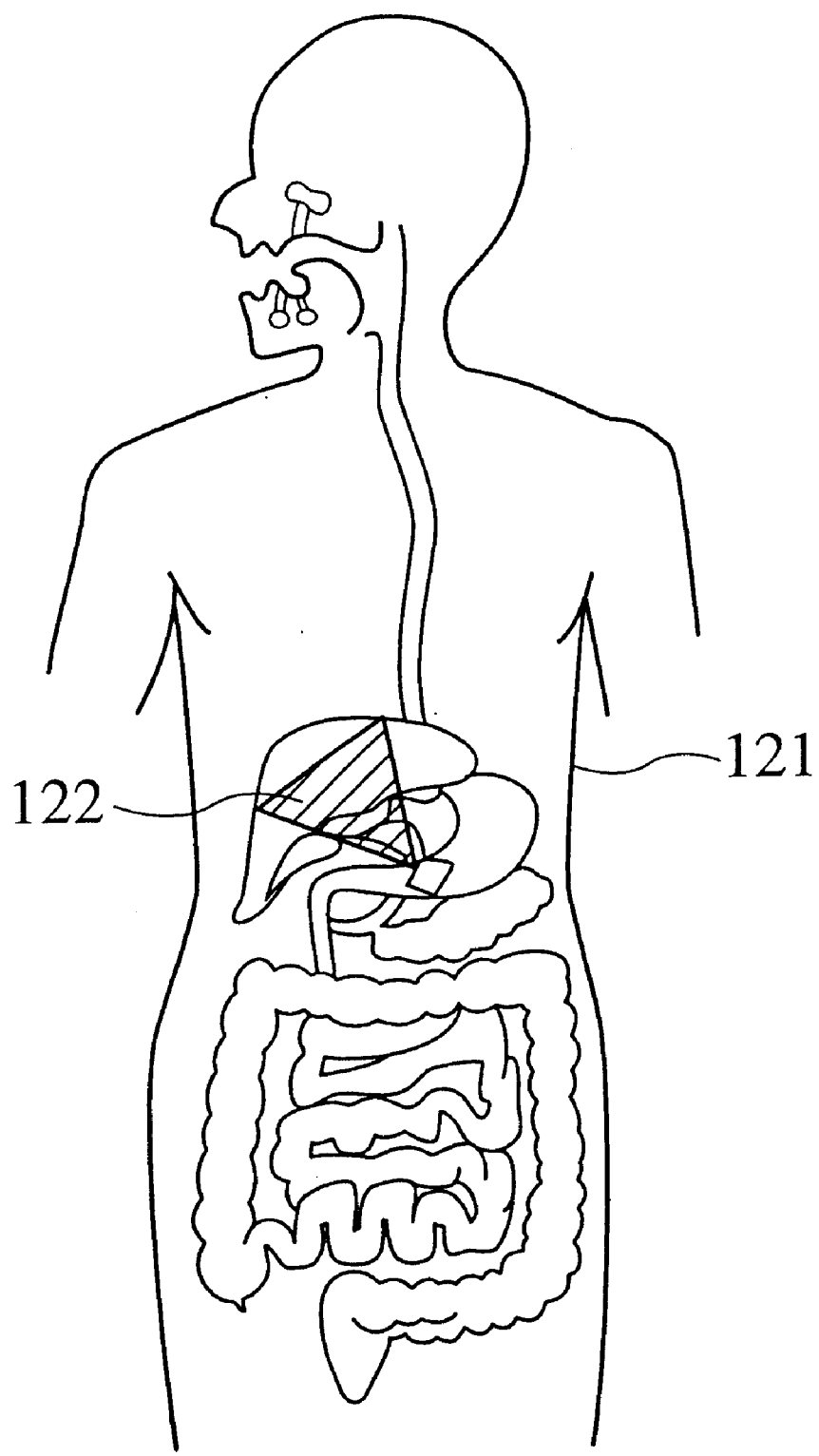
FIG. 12 is a view for explaining one example of a body mark attached display according to the fifth embodiment of the present invention.
Figure 13A:
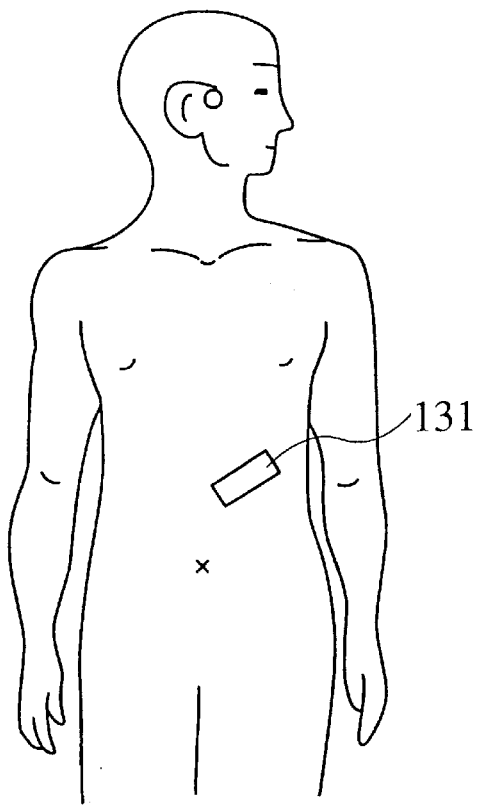
FIGS. 13A, 13B and 13C are views for explaining another example of a body mark attached display according to the fifth embodiment of the present invention.
Figure 13B:
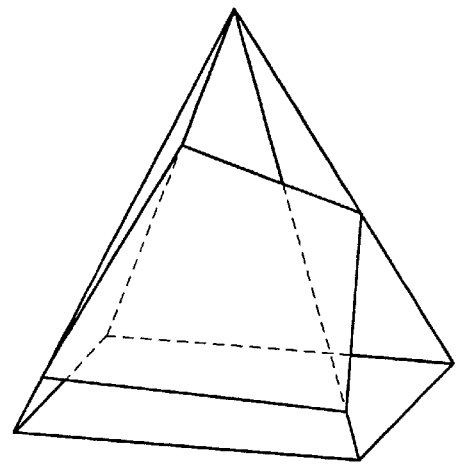
Figure 13C:
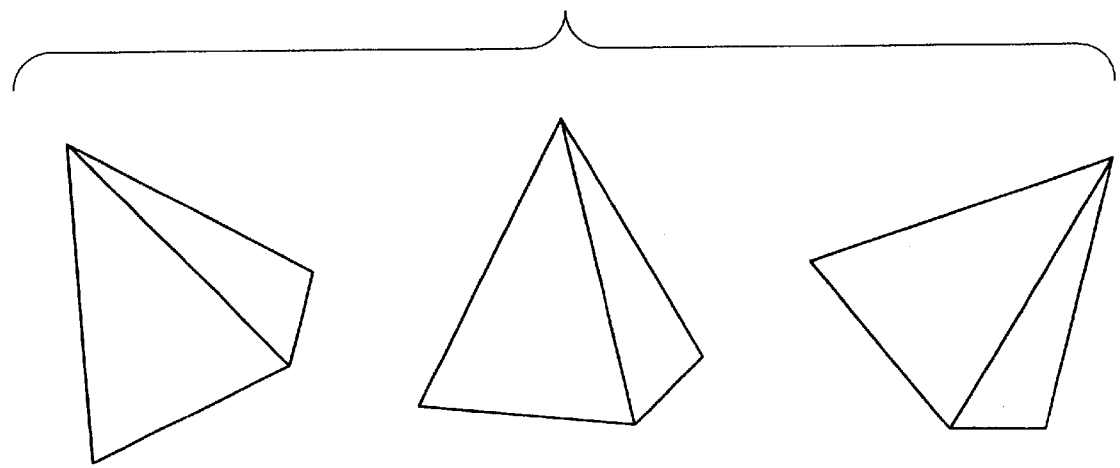

FIG. 12 and FIG. 13 illustrate detailed examples of a body mark display. FIG. 12 shows an example of displaying an indicator 122 that shows a display area or a display cross section on a display 121 of a model diagram illustrating a human body. FIG. 13A shows an example of displaying an indicator 131 that shows a position of a probe on the diagram of a human body model. In parallel with this display, there may be displayed an indicator shown in FIG. 13B or FIG. 13C that illustrates a direction of a three-dimensional area being acquired. It is also possible to set the above initial position (for example, a data acquisition starting position) by using an input device such as a track ball or a mouse together with the human body model 121 as shown in FIG. 12.

Further, when both the above-described body mark data and the volume data are utilized, it is possible to compare volume data acquired at the same part and acquired at different times. More specifically, a plurality of three-dimensional image data (volume data) acquired at different times and at the same part are searched based on the body mark data. Then, based on the position data of the volume data, it is possible to carry out, for example, a parallel display or a superimposed display of images (three-dimensional display images or arbitrary tomographic images) from the same viewpoint. This facilitates the observation by the observer.

According to the fifth embodiment, the following effects can be obtained. The position detecting mechanism such as the probe position sensor 30 or the position detector 31 records position data corresponding to each volume data in the position data memory 32. The image processor 7 connects a plurality of volume data by using this position data, and displays the connected image, or displays a body mark on the three-dimensional display image. Therefore, it is possible to display a three-dimensional display image of high image quality over a wider range.

In the above explanation of the fifth embodiment, the correction process using the position data is carried out as a post processing to acquired data after the data acquisition. However, the data may be corrected in real time, and the result is displayed, when this procedure can be permitted by hardware performance. Further, although a position sensor 30 has been used as a position detecting mechanism of the three-dimensional ultrasonic probe 1, the kind is not particularly limited so long as necessary precision is obtained. When it is possible to detect a scanning position, it may be so arranged that the position of the three-dimensional ultrasonic probe 1 is detected by the above-described image processing without using a position sensor 30.

Sixth Embodiment

Next, a three-dimensional ultrasonic diagnostic apparatus according to a sixth embodiment of the present invention will be explained in detail with reference to FIG. 14. The sixth embodiment provides a function of selecting either a display condition used for the display in the past or a display condition currently set in the image processor 7, at the time of replay of a three-dimensional display image based on volume data stored in the four-dimensional volume memory 5.

Figure 14:
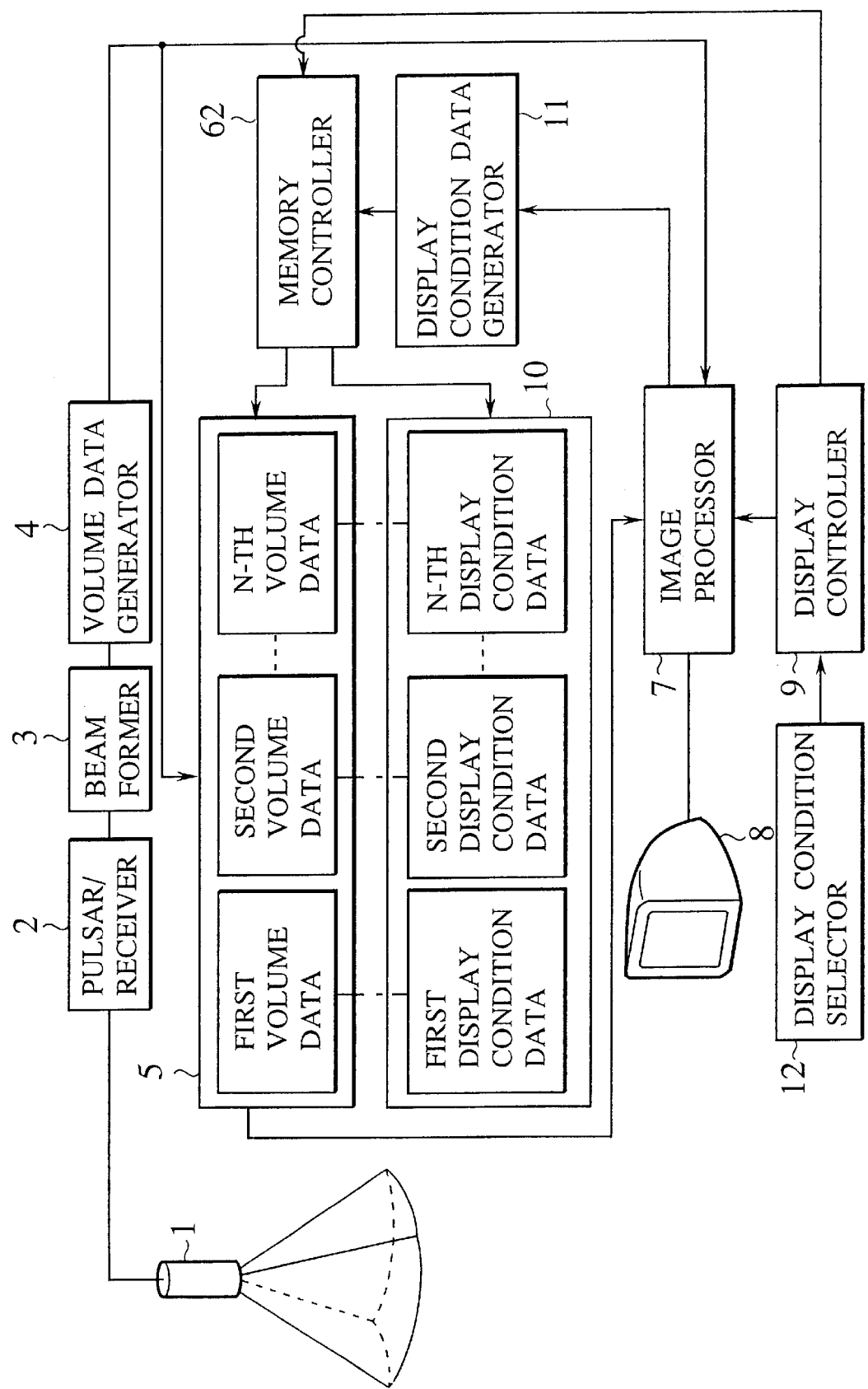
FIG. 14 is a block diagram for showing a structure of a three-dimensional ultrasonic diagnostic apparatus according to a sixth embodiment of the present invention.

FIG. 14 is a block diagram for showing a structure of the three-dimensional ultrasonic diagnostic apparatus according to the sixth embodiment of the present invention.

The sixth embodiment is a modification of the second embodiment in that, as compared with the second embodiment shown in FIG. 2, the apparatus further includes a display condition selector 12 for selecting either a display condition used for the display in the past or a display condition currently set. As the six embodiment is different from the second embodiment in only the above point, description will be made hereinafter of only this difference, and a duplicated explanation will be omitted. In FIG. 14, those units attached with reference symbols identical with those in FIG. 2 provide similar functions as those of the corresponding units of the same reference symbols.

Next, the process procedure of the three-dimensional ultrasonic diagnostic apparatus according to the sixth embodiment will be explained. The operations of the three-dimensional ultrasonic probe 1, the pulsar/receiver 2, the beam former 3 and the volume data generator 4 are similar to those of the above embodiment.

In the three-dimensional ultrasonic diagnostic apparatus according to the sixth embodiment, when the operator replays a three-dimensional display image based on arbitrary three-dimensional volume data in the four-dimensional volume memory 5 through the memory controller 9, the display condition selector 12 selects either the display condition data in the display condition data memory 10 stored corresponding to the volume data or the display condition information currently being set in the image processor 7. The operator instructs by input the selection of this display condition information.

The volume data read out from the memory controller 62 is image-processed by the image processor 7 based on the display condition selected by the display condition selector 12, and the image-processed result is displayed on the display unit 8.

According to the sixth embodiment, the following effects can be obtained. In reconstructing a three-dimensional display image based on the volume data obtained from the four-dimensional volume memory 5, the display condition selector 12 instructs to the display controller 9 about which one of the display condition data is to be used from among the one used when the volume data was displayed in the past and the one currently being set in the image processor 7. Therefore, the operator can easily obtain a past three-dimensional display image under the display condition used in the past (at the time of adjusting the image), without involving a complex operation for image adjustment at the time of replay of a three-dimensional display image based on the past volume data. According to the need, it is also possible to suitably adjust an image for analysis using the display condition currently being set. Therefore, the operator can further carry out a variety of three-dimensional image analyses in an easy operation.

It should be noted that the above-described first to the sixth embodiments can be structured by suitably combining these embodiments, in addition to the structures as described above.

In summary, according to the above-described embodiments, the four-dimensional volume memory 5 sequentially stores in time series a plurality of pieces of three-dimensional image data (volume data). Therefore, it is possible to easily carry out various three-dimensional image analyses retroactively. Further, the display condition data memory 10 sequentially stores display condition data of the three-dimensional display image real-time displayed in the past, with making this display condition data correspond to each volume data. Accordingly, it is possible to retroactively replay the three-dimensional image displayed in the past, in a simple operation, without involving a complex image adjusting operation. As a result, a variety of three-dimensional image analyses can be made much easier. Further, the display image memory 15 continuously stores in time series three-dimensional display images displayed in real time, together with the four-dimensional volume memory 5 for storing three-dimensional image data in time series. Therefore, it is possible to replay at high speed a three-dimensional image displayed in the past. This further facilitates various three-dimensional image analyses. When these memories (the four-dimensional volume memory 5, the display condition data memory 10 and the display image memory 15) are used, it is possible to continuously replay past three-dimensional display images at high speed under a complex setting condition newly set to the past three-dimensional image information, as well as the display of the past images displayed in real time in the past.

Furthermore, when position data of a scanning range is added to three-dimensional image data by providing the position detector 31 for an ultrasonic scanning range, it is possible to understand a relative positional relationship between three-dimensional image data continuously stored in the time axis. Thus, it is possible to display a three-dimensional image to be reconstructed over a wider range, in high precision and in a manner to be able to analyze the image easily.

It is to be noted that, besides those already mentioned above, may modifications and variations of the above embodiments many be made without departing from the novel and advantageous features of the present invention. Accordingly, all such modifications and variations are intended to be included within the scope of the appended claims.

What is claimed is:

1. An ultrasonic diagnostic apparatus, comprising:
   a three-dimensional scanner for carrying out a three-dimensional scanning by ultrasonic waves;
   a three-dimensional volume data former for forming three-dimensional volume data acquired through the three-dimensional scanning;
   a three-dimensional volume data memory for storing in time series a plurality of pieces of three-dimensional volume data from which display image is to be reconstructed;

a display condition data former for forming display condition data indicating a direction of a projection and how the display image is displayed on a display unit;

a display condition data memory for storing in time series a plurality of pieces of display condition data, each of which corresponds to each of the three-dimensional volume data stored in the three-dimensional volume data memory and used to reconstruct the display image;

a memory controller for controlling write and read of the stored three-dimensional volume data and display condition data; and a display image processor for reconstructing display images based on three-dimensional volume data read out from the three-dimensional volume data memory and corresponding display condition data by the memory controller, and for displaying the reconstructed display image on a display unit.

2. The apparatus according to claim 1, further comprising:

a display condition selector for selecting either the display condition data used in the past to form a display image from the three dimensional volume data or the currently-set display condition data, according to a user's instruction, wherein the display image processor reconstructs a display image based on the read-out three-dimensional volume data, according to the display condition data selected by the display condition selector.

3. The apparatus according to claim 1, wherein the display condition data includes at least one of a direction of viewpoint, opacity, color information added to a Doppler image, and a threshold value for extracting an area of the subject.

4. The apparatus according to claim 1, further comprising:

a display image memory for storing in time series a plurality of the display images, each of the display images being stored in association with each of the three-dimensional volume data.

5. The apparatus according to claim 4, wherein the display image memory is structured by a loop memory for sequentially storing a prescribed number of pieces of display image, and the memory controller writes the latest display image on the oldest display image in the display image memory when a number of pieces of display image to be written in the display image memory exceeds the prescribed number of pieces of display image.

6. The apparatus according to claim 1, further comprising:

a display image memory for storing in time series a plurality of the display images, each of the display images being stored in association with each of the three-dimensional volume data.

7. The apparatus according to claim 1, further comprising:

a position data generator for generating probe position data according to a position of the three-dimensional scanner; and a position data memory for storing in time series the probe position data obtained from the position data generator with making the probe position data correspond to each of the three-dimensional volume data stored in the three-dimensional volume data memory.

8. The apparatus according to claim 7, wherein the display image processor reconstructs a display image of a wider range than that of each of the three-dimensional volume data by connecting a plurality of pieces of three-dimensional volume data stored in the three-dimensional volume data memory, according to the probe position data.

9. The apparatus according to claim 7, wherein the display image processor reconstructs a display image with corrected image quality of each three-dimensional volume data by combining a plurality of pieces of three-dimensional volume data stored in the three-dimensional volume data memory, according to the probe position data.

10. The apparatus according to claim 7, wherein the display image processor calculates a relative position for indicating what portion of a subject a display image corresponds to, according to reference position data for indicating a position of the three-dimensional scanner set on the subject and the probe position data, and displays on the display an indicator for showing the relative position based on the calculated relative position together with the display image.

11. The apparatus according to claim 7, wherein the position data memory is structured by a loop memory for sequentially storing a prescribed number of pieces of probe position data, and the memory controller writes the latest probe position data on the oldest probe position data in the position data memory when a number of pieces of probe position data to be written in the position data memory exceeds the prescribed number of pieces of probe position data.

12. The apparatus according to claim 1, wherein the three-dimensional volume data memory is structured by a loop memory for sequentially storing a prescribed number of pieces of three-dimensional volume data, and the memory controller writes the latest three-dimensional volume data on the oldest three-dimensional volume data in the three-dimensional volume data memory when a number of pieces of three-dimensional volume data to be written in the three-dimensional volume data memory exceeds the prescribed number of pieces of three-dimensional volume data.

13. The apparatus according to claim 12, wherein the loop memory is structured to include a first memory for storing tomographic image information of a subject and a second memory for storing Doppler information of a tissue inside the subject.

14. The apparatus according to claim 1, wherein the display condition data memory is structured by a loop memory for sequentially storing a prescribed number of pieces of display condition data, and the memory controller writes the latest display condition data on the oldest display condition data in the display condition data memory when a number of pieces of display condition data to be written in the display condition data memory exceeds the prescribed number of pieces of display condition data.

15. The apparatus according to claim 1, wherein the display image processor reconstructs a display image based on three-dimensional volume data read out from the three-dimensional volume data memory by the memory controller, or sequentially reconstructs three-dimensional volume data provided by the three-dimensional volume data former into a display image.

16. An ultrasonic diagnostic apparatus using a three-dimensional display image, comprising:

a three-dimensional scanner for carrying out a three-dimensional scanning by ultrasonic waves;

a three-dimensional volume data former for forming three-dimensional volume data acquired through the three-dimensional scanning;

a four-dimensional memory for storing in time series a plurality of pieces of three-dimensional volume data from which display image is to be reconstructed;

a display condition data former for forming display condition data indicating a direction of a projection and how the display image is displayed on a display unit;

a display condition data memory for storing in time series a plurality of pieces of display condition data, each of which corresponds to each of the three-dimensional volume data stored in the four-dimensional volume data memory and used to reconstruct the display image;

a memory controller for controlling write and read of the stored three-dimensional volume data and display condition data memory; and a display image processor for reconstructing display images based on three-dimensional volume data read out from the four-dimensional memory and corresponding display condition data by the memory controller, and for displaying the reconstructed display image on a display unit.

17. An ultrasonic diagnostic apparatus, comprising:

a three-dimensional scanner for carrying out a three-dimensional scanning by ultrasonic waves;

a three-dimensional volume data former for forming three-dimensional volume data acquired through the three-dimensional scanning;

a three-dimensional volume data memory for storing in time series a plurality of pieces of three-dimensional volume data from which display image is to be reconstructed;

a display condition data former for forming display condition data indicating a direction of a projection and how the display image is displayed on a display unit;

a display condition data memory for storing in time series a plurality of pieces of display condition data, each of which corresponds to each of the three-dimensional volume data stored in the three-dimensional volume data memory and used to reconstruct the display image;

a memory controller for controlling write and read of the stored three-dimensional volume data and the display condition data into or from the three-dimensional volume data memory and the display condition data memory respectively; and a display image processor for reconstructing display images based on three-dimensional volume data read out from the three-dimensional volume data memory and corresponding display condition data read out from the display condition data memory by the memory controller, and for displaying the reconstructed display image on a display unit.

18. An ultrasonic diagnostic apparatus, comprising:

a three-dimensional scanner for carrying out a three-dimensional scanning by ultrasonic waves;

a three-dimensional image data former for forming three-dimensional image data based on scanning data obtained from the three-dimensional scanner;

a three-dimensional image data memory for storing in time series a plurality of pieces of three-dimensional image data formed by the three-dimensional image data former;

a memory controller for controlling write and read of the three-dimensional image data into or from the three-dimensional image data memory;

a display image former for forming a display image based on three-dimensional image data read out from the three-dimensional image data memory by the memory controller, and for displaying the formed display image on a display unit;

a position data generator for generating probe position data according to a position of the three-dimensional scanner; and a position data memory for storing in time series the probe position data obtained from the position data generator with making the probe position data correspond to each of the three-dimensional image data stored in the three-dimensional image data memory.

19. The apparatus according to claim 18, wherein the display image former forms a display image of a wider range than that of each of the three-dimensional image data by connecting a plurality of pieces of three-dimensional image data stored in the three-dimensional image data memory, according to the probe position data.

20. The apparatus according to claim 18, wherein the display image former forms a display image with corrected image quality of each three-dimensional image data by combining a plurality of pieces of three-dimensional image data stored in the three-dimensional image data memory, according to the probe position data.

21. The apparatus according to claim 18, wherein the display image former calculates a relative position for indicating what portion of a subject a display image corresponds to, according to reference position data for indicating a position of the three-dimensional scanner set on the subject and the probe position data, and displays on the display an indicator for showing the relative position based on the calculated relative position together with the display image.

22. The apparatus according to claim 18, wherein the position data memory is structured by a loop memory for sequentially storing a prescribed number of pieces of probe position data, and the memory controller writes the latest probe position data on the oldest probe position data in the position data memory when a number of pieces of probe position data to be written in the position data memory exceeds the prescribed number of pieces of probe position data.

23. An ultrasonic diagnostic apparatus, comprising:

a three-dimensional scanner for carrying out a three-dimensional scanning by ultrasonic waves;

a three-dimensional image data former for forming three-dimensional image data based on scanning data obtained from the three-dimensional scanner;

a three-dimensional image data memory for storing in time series a plurality of pieces of three-dimensional image data formed by the three-dimensional image data former;

a memory controller for controlling write and read of the three-dimensional image data into or from the three-dimensional image data memory; and a display image former for forming a display image based on three-dimensional image data read out from the three-dimensional image data memory by the memory controller, and for displaying the formed display image on a display unit, wherein the three-dimensional image data memory is structured by a loop memory for sequentially storing a prescribed number of pieces of three-dimensional image data, and the memory controller writes the latest three-dimensional image data on the oldest three-dimensional image data in the three-dimensional image data memory when a number of pieces of three-dimensional image data to be written in the three-dimensional image data memory exceeds the prescribed number of pieces of three-dimensional image data.

24. The apparatus according to claim 23, wherein the loop memory is structured to include a first memory for storing tomographic image information of a subject and a second memory for storing Doppler information of a tissue inside the subject.

25. An ultrasonic diagnostic apparatus, comprising:

a three-dimensional scanner for carrying out a three-dimensional scanning by ultrasonic waves;

a three-dimensional image data former for forming three-dimensional image data based on scanning data obtained from the three-dimensional scanner;

a three-dimensional image data memory for storing in time series a plurality of pieces of three-dimensional image data formed by the three-dimensional image data former;

a memory controller for controlling write and read of the three-dimensional image data into or from the three-dimensional image data memory;

a display image former for forming a display image based on three-dimensional image data read out from the three-dimensional image data memory by the memory controller, and for displaying the formed display image on a display unit; and a display condition data memory for storing in time series a plurality of pieces of display condition data for forming the display image, the display condition data being corresponding to each of the tree-dimensional image data, wherein the display condition data memory is structured by a loop memory for sequentially storing a prescribed number of pieces of display condition data, and the memory controller writes the latest display condition data on the oldest display condition data in the display condition data memory when a number of pieces of display condition data to be written in the display condition data memory exceeds the prescribed number of pieces of display condition data.

26. An ultrasonic diagnostic apparatus, comprising:

a three-dimensional scanner for carrying out a three-dimensional scanning by ultrasonic waves;

a three-dimensional image data former for forming three-dimensional image data based on scanning data obtained from the three-dimensional scanner;

a three-dimensional image data memory for storing in time series a plurality of pieces of three-dimensional image data formed by the three-dimensional image data former;

a memory controller for controlling write and read of the three-dimensional image data into or from the three-dimensional image data memory;

a display image former for forming a display image based on three-dimensional image data read out from the three-dimensional image data memory by the memory controller, and for displaying the formed display image on a display unit; and a display image memory for storing in time series a plurality of the display images, each of the display images being corresponding to the three-dimensional image data, wherein the display image memory is structured by a loop memory for sequentially storing a prescribed number of pieces of display image, and the memory controller writes the latest display image on the oldest display image in the display image memory when a number of pieces of display image to be written in the display image memory exceeds the prescribed number of pieces of display image.

\* \* \* \* \*